(12) United States Patent
Wang et al.

(10) Patent No.: US 10,548,709 B2
(45) Date of Patent: Feb. 4, 2020

(54) AORTIC ARCH INTRAOPERATIVE STENT AND MANUFACTURING METHOD THEREOF

(71) Applicant: Lifetech Scientific (Shenzhen) Co., Ltd., Shenzhen (CN)

(72) Inventors: Yongsheng Wang, Shenzhen (CN); Zhiyun Xu, Shenzhen (CN); Deyuan Zhang, Shenzhen (CN); Caiping Liu, Shenzhen (CN); Benhao Xiao, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 23 days.

(21) Appl. No.: 15/108,287

(22) PCT Filed: Dec. 30, 2014

(86) PCT No.: PCT/CN2014/095609
§ 371 (c)(1),
(2) Date: Jun. 24, 2016

(87) PCT Pub. No.: WO2015/101292
PCT Pub. Date: Jul. 9, 2015

(65) Prior Publication Data
US 2016/0310258 A1    Oct. 27, 2016

(30) Foreign Application Priority Data
Dec. 30, 2013   (CN) .......................... 2013 1 0745529

(51) Int. Cl.
*A61F 2/07*   (2013.01)
*A61F 2/844*  (2013.01)
(Continued)

(52) U.S. Cl.
CPC ............... *A61F 2/07* (2013.01); *A61F 2/844* (2013.01); *A61F 2/915* (2013.01);
(Continued)

(58) Field of Classification Search
CPC ....................................................... A61F 2/07
See application file for complete search history.

(56) References Cited

U.S. PATENT DOCUMENTS 3,479,670 A * 11/1969 Medell ...................... A61F 2/06
                                                            134/125
4,731,073 A *  3/1988 Robinson .................. A61F 2/06
                                                            623/1.44
(Continued)

FOREIGN PATENT DOCUMENTS

CN         2922835 Y    7/2007
CN       200960184 Y   10/2007
(Continued)

OTHER PUBLICATIONS

PCT Search Report for corresponding PCT application No. PCT/CN2014/095609.
(Continued)

*Primary Examiner* — Jacqueline Woznicki
(74) *Attorney, Agent, or Firm* — Raymond Sun

(57) ABSTRACT

The present invention provides an aortic arch intraoperative stent, wherein the aortic arch intraoperative stent comprising a main body (17) and one to three branches (5, 6, 7), The aortic arch intraoperative stent connects several circular waveform rings together via a cover membrane (25) to form the main body (17) and the branches (5, 6, 7), wherein each circular waveform ring comprises a circular elastic wire formed through head-to-tail connection. In addition, the present invention also provides a manufacturing method for the aortic arch intraoperative stent, comprising the following
(Continued)

steps of: providing a cover membrane mandrel (40); making an inner membrane; assembling circular waveform rings; making an outer membrane; suturing a proximal fabric (12); and suturing a distal fabric (13). The aortic arch intraoperative stent can automatically adapt to the vascular structure near the aortic arch of different patients, and the main body (17) in the aortic arch intraoperative stent maintains a sufficient radial support for the branches, thereby ensuring that the branches on the aortic arch intraoperative stent may safely enter branch vessels during surgery, and preventing the branches from slipping out of the corresponding branch vessels during and after surgery at the same time.

18 Claims, 12 Drawing Sheets

(51) Int. Cl.
*A61F 2/915* (2013.01)
*A61F 2/06* (2013.01)

(52) U.S. Cl.
CPC ... *A61F 2002/061* (2013.01); *A61F 2002/072* (2013.01); *A61F 2002/075* (2013.01); *A61F 2002/91583* (2013.01); *A61F 2210/0076* (2013.01)

(56) References Cited

U.S. PATENT DOCUMENTS

| | | | | |
|---|---|---|---|---|
| 5,123,917 A | * | 6/1992 | Lee | A61F 2/86 623/1.13 |
| 5,667,523 A | * | 9/1997 | Bynon | A61F 2/07 606/194 |
| 5,693,085 A | * | 12/1997 | Buirge | A61F 2/0022 606/192 |
| 5,827,321 A | * | 10/1998 | Roubin | A61F 2/91 606/195 |
| 6,010,529 A | * | 1/2000 | Herweck | A61F 2/06 600/36 |
| 2004/0193244 A1 | * | 9/2004 | Hartley | A61F 2/06 623/1.12 |
| 2005/0027347 A1 | * | 2/2005 | Chobotov | B29C 53/44 623/1.13 |
| 2006/0100695 A1 | * | 5/2006 | Peacock, III | A61F 2/91 623/1.42 |
| 2007/0167955 A1 | * | 7/2007 | Arnault De La Menardiere | A61F 2/954 606/108 |
| 2011/0270379 A1 | | 11/2011 | Bruszewski et al. | |

FOREIGN PATENT DOCUMENTS

| | | |
|---|---|---|
| CN | 201026247 Y | 2/2008 |
| CN | 202122626 U | 1/2012 |
| CN | 102525702 A | 7/2012 |
| CN | 102641164 A | 8/2012 |
| CN | 102670338 A | 9/2012 |
| CN | 103462726 A | 12/2013 |
| CN | 103720529 A | 4/2014 |
| WO | WO02076346 A1 | 10/2000 |
| WO | WO2011136940 A1 | 11/2011 |
| WO | WO2013022549 A1 | 2/2013 |

OTHER PUBLICATIONS

First office action in corresponding European application No. 14 876 566.2.
First office action in corresponding China application No. 201310745529.1.
Second office action in corresponding China applicaton No. 201310745529.1.
Third office action in corresponding China application No. 201310745529.1.

* cited by examiner

AORTIC ARCH INTRAOPERATIVE STENT AND MANUFACTURING METHOD THEREOF

TECHNICAL FIELD

The present invention relates to the technical field of medical equipment, in particular to an intraoperative stent applied to a hybrid operation treatment for the aortic arch of human body, and manufacturing method thereof

BACKGROUND OF THE PRESENT INVENTION

Aortic dissection refers to the intima being gradually stripped and expanded under the powerful impact of blood due to a local intimal tear to form a true lumen and a false lumen in the artery. According to Stanford categorization method, the aortic dissection comprises type A and type B: type A aortic dissection refers to an intimal tear that is located at the ascending aorta, the aortic arch or the proximal descending aorta, expanded involving the ascending aorta or the aortic arch, and may also be expanded to the descending aorta and even to the abdominal aorta; type B aortic dissection refers to an intimal tear that is located at the aortic isthmus, and expanded only involving the descending aorta or extended to the abdominal aorta without involving the ascending aorta and the aortic arch. At present, the treatment method for the type A aortic dissection is mainly surgery or hybrid operation; compared with the traditional surgery, the hybrid operation has been partially simplified, but how to further simplify the operation, shorten the time, reduce the amount of bleeding during surgery, and shorten the time of blood interruption in the brain is currently a major explorative subject. The complex anatomical structure of the aortic arch and more vascular anastomotic stomas during surgery are some of the main reasons leading to complex and long-duration surgery; it is a feasible strategy to try to reduce the number of the anastomotic stomas through a stent releasing method. Therefore, a stent with branches according to the anatomical shape of the aortic arch is required; however, the stent is to be implanted in three branch vessels which respectively are the left subclavian artery, the left internal carotid artery and the innominate artery. Due to the specificity of the anatomical shape of the aortic arch of human body, the fact that the three branch vessels ensure normal blood supply for the upper limbs and brain, and the fact that the spacing distance among the three branch vessels varies with each individual, the difficulty with surgery is to ensure that the intraoperative stent safely enters the three branches of the corresponding branch vessels, and will not be displaced and slipped out during and after surgery. If the branches of the intraoperative stent are displaced and slipped out of the branch vessels, it will cause serious consequences.

SUMMARY OF THE PRESENT INVENTION

An object of the present invention is to provide an aortic arch intraoperative stent used for treating the type A aortic dissection located at the aortic arch through hybrid operation, aiming to solve the problems of providing a safe and reliable aortic arch intraoperative stent which automatically adapts to the vascular structure near the aortic arch of different patients and ensures that the intraoperative stent may be safely implanted to the aortic arch main body and branch vessels during surgery, so that all positions of the intraoperative stent will not have displacement, internal hemorrhage, and the like, after surgery.

The present invention is achieved by providing an aortic arch intraoperative stent, including a main body and one to three branches communicated to the main body; the main body includes self-expansion second circular waveform rings corresponding to one to three branches one by one, and each branch includes at least one self-expansion third circular waveform ring; an intersecting line of each branch and the main body is overlapped with at least one part of a region where the second circular waveform ring corresponding to the branch is located; the aortic arch intraoperative stent further includes a cover membrane for connecting all the second circular waveform rings and the third circular waveform rings into a whole body.

In the aortic arch intraoperative stent according to the embodiment of the present invention, the main body includes an arch segment and a descending aorta segment, the branches are located at the arch segment; the descending aorta segment includes a plurality of first circular waveform rings arranged in spaced-apart manner along the axial direction of the main body; first connection rods, which are linear and located on the same side as the branches of the main body, are connected between at least one part of the first circular waveform rings.

In the aortic arch intraoperative stent according to the embodiment of the present invention, the diameters of the first circular waveform rings are equal, or gradually decreased along the direction from a proximal end to a distal end.

In the aortic arch intraoperative stent according to the embodiment of the present invention, one branch closest to the descending aorta segment includes a plurality of third circular waveform rings arranged in spaced-apart manner, an L-shaped second connection rod is arranged on one side of the branch close to the descending aorta segment, a long arm of the second connection rod connects at least one part of the third circular waveform rings on the branch together, and a short arm thereof is fixed on the first connection rod or on the first circular waveform ring corresponding to the branch.

In the aortic arch intraoperative stent according to the embodiment of the present invention, a waveform of the second circular waveform ring encircles the intersecting line of the corresponding branch and the main body.

In the aortic arch intraoperative stent according to the embodiment of the present invention, the branch includes a plurality of third circular waveform rings that are arranged in spaced-apart manner, and an L-shaped second connection rod or a linear third connection rod; the long arm of the second connection rod or the third connection rod connects at least one part of the third circular waveform rings together, the short arm of the second connection rod is fixed on the second circular waveform ring corresponding to the branch, and the second connection rod is located at one side of the branch close to the proximal end of the main body.

In the aortic arch intraoperative stent according to the embodiment of the present invention, at least one part of a projection line of the intersecting line is embedded in a projection line region in the same direction as the waveform which encircles the intersecting line, a ratio of the embedded height to the corresponding height of the embedded projection line region is at least 1:2, or, at least half area of the projection line region of the intersecting line is embedded in the projection line region in the same direction as the waveform which encircles the intersecting line.

In the aortic arch intraoperative stent according to the embodiment of the present invention, at least one part of the projection line of the intersecting line of one branch closest to the proximal end is embedded in the projection line region in the same direction as the waveform which encircles the intersecting line, and an axial relative height between the closest end of the projection line region and the closest end of the projection line is 3 to 8 mm.

In the aortic arch intraoperative stent according to the embodiment of the present invention, the branch includes a plurality of third circular waveform rings, wherein a shortest distance between one of the third circular waveform rings closest to the main body and the main body is 4 to 10 mm.

In the aortic arch intraoperative stent according to the embodiment of the present invention, one of the third circular waveform rings farthest from the main body has the smallest waveform height and the largest waveform number.

In the aortic arch intraoperative stent according to the embodiment of the present invention, the branch includes a plurality of third circular waveform rings, the diameters of the plurality of third circular waveform rings are gradually decreased along the axial direction from one end of the branch connected to the main body, and one end of the branch far from the main body is necked down.

In the aortic arch intraoperative stent according to the embodiment of the present invention, the branch includes a plurality of third circular waveform rings, the diameters of the plurality of third circular waveform rings are gradually decreased along the axial direction from one end of the branch far from the main body, and one end of the branch connected to the main body is necked down.

In the aortic arch intraoperative stent according to the embodiment of the present invention, the cover membrane is made of expanded polytetrafluoroethylene and includes an inner membrane and an outer membrane, the inner membrane and the outer membrane are combined to cover all the circular waveform rings between them.

In the aortic arch intraoperative stent according to the embodiment of the present invention, the cover membrane is made of polyester fabric, all the circular waveform rings are sutured on an outer side or an inner side of a tubular wall of the cover membrane.

In the aortic arch intraoperative stent according to the embodiment of the present invention, when the aortic arch intraoperative stent includes at least two second circular waveform rings, the second circular waveform rings are connected to each other without using a connection rod.

In the aortic arch intraoperative stent according to the embodiment of the present invention, a shortest distance between the two adjacent second circular waveform rings is 2 to 8 mm.

In the aortic arch intraoperative stent according to the embodiment of the present invention, a first layer of tubular proximal fabric is arranged on the proximal end of the main body, the first layer of the proximal fabric includes a first segment located at the proximal end side and a second segment located at the distal end side; the second segment covers part of the main body and is connected to the main body into a whole body, and the first segment is a free segment; the diameter of the first segment is smaller than that of the second segment.

In the aortic arch intraoperative stent according to the embodiment of the present invention, a tubular distal fabric, which is connected to the cover membrane into a whole body and fixed on the first circular waveform ring, is arranged on the distal end of the main body, the distal fabric is aligned with an end face of the distal end or the distal fabric extends out of the distal end.

In the aortic arch intraoperative stent according to the embodiment of the present invention, the first layer of the proximal fabric is prepared from ribbed polyester fabric.

In the aortic arch intraoperative stent according to the embodiment of the present invention, the distal end of the second segment is located at the distal end side of the branch.

In the aortic arch intraoperative stent according to the embodiment of the present invention, a proximal inner wall of the main body is further fixed and covered with a second layer of proximal fabric, the proximal end of the second proximal fabric is overturned outward at a proximal edge of the main body and fixedly covers on the proximal edge of the main body.

In the aortic arch intraoperative stent according to the embodiment of the present invention, the proximal end of the main body further includes a third layer of proximal fabric covering at least one part of the second segment, the proximal end of the third proximal fabric layer is aligned with the proximal edge of the main body.

The present invention further provides a manufacturing method of the aortic arch intraoperative stent, including the following steps of:

S1) providing a cover membrane mandrel which includes a first column and second columns connected to a side wall of the first column, the number of the second columns being the same as that of the branches in the aortic arch intraoperative stent;

S2) integrally forming an inner membrane of a cover membrane on an overall outer surface of the cover membrane mandrel;

S3) providing second circular waveform rings corresponding to the second columns one by one and a plurality of third circular waveform rings, wherein each second circular waveform ring is sleeved on the first column, so that an intersecting line of the first column and the second column is overlapped with at least one part of a region where the second circular waveform ring corresponding to the second column is located, one of the third circular waveform rings is at least sleeved on each second column; and S4) suturing and fixing the second circular waveform rings and the third circular waveform rings on the inner membrane, taking the inner membrane as the cover membrane; or integrally forming an outer membrane of the cover membrane on the overall outer surface of the cover membrane mandrel, and fixing and attaching the inner membrane and the outer membrane to cover the circular waveform rings.

The present invention further provides a manufacturing method of the aortic arch intraoperative stent, including the following steps of:

S1) providing a cover membrane mandrel which includes a first column and second columns connected to a side wall of the first column, the number of the second columns being the same as that of the branches in the aortic arch intraoperative stent;

S2) providing second circular waveform rings corresponding to the second columns one by one and a plurality of third circular waveform rings, wherein each second circular waveform ring is sleeved on the first column, so that an intersecting line of the first column and the second column is overlapped with at least one part of a region where the second circular waveform ring corresponding to the second column is located, one of the third circular waveform rings is at least sleeved on each second column;

S3) sleeving a cover membrane on the outer surface of the cover membrane mandrel; and S4) suturing the cover membrane and the circular waveform rings.

The manufacturing method of the aortic arch intraoperative stent of the embodiment of the present invention further includes a step after S4):

S5) covering and suturing a first layer of tubular proximal fabric on the cover membrane of the proximal end of the first column, wherein the first layer of the proximal fabric includes a first segment located at the proximal end side and a second segment located at the distal end side; the second segment covers part of the main body and is fixedly connected to the main body into a whole body, and the first segment is a free segment; the diameter of the first segment is smaller than that of the second segment.

In the manufacturing method of the aortic arch intraoperative stent of the embodiment of the present invention, at least one axial first column is arranged on the distal end of the second segment.

Compared with the prior art, the present invention has the following technical effects: the aortic arch intraoperative stent provided by the present invention may automatically adapt to the vascular structure near the aortic arch of different patients, and the main body in the aortic arch intraoperative stent maintains a sufficient radial support for the branches, thereby ensuring that the branches on the aortic arch intraoperative stent may safely enter branch vessels during surgery, and preventing the branches from slipping out of the corresponding branch vessels during and after surgery at the same time. The aortic arch intraoperative stent provided by the present invention has the following advantages.

1) The main body of the aortic arch intraoperative stent in the present invention provides a reliable support for the branches, thereby ensuring that the branches may completely enter branch vessels, and preventing the stent from displacing and slipping out postoperative in the future.

2) Due to the complex anatomical structure of the aortic arch, the individual difference in the distance between the three branches of different patients is relatively large. However, the type A aortic dissection of the aortic arch is usually an emergency, so there is insufficient time for a patient to customize a special product which is exactly matched with the distance between the three branches of the patient. The distance between the branches of the aortic arch intraoperative stent of the present invention may be adaptively adjusted according to the anatomical shape of the aortic arch, thereby solving the problem of matching the aortic arch intraoperative stent in emergency surgery due to relatively large individual difference in the shape of the aortic arch of the patients.

3) The main body and the branches of the aortic arch intraoperative stent in the present invention may adopt a double-layer membrane covering technology of integral inner and outer layers of ePTFE (Expanded Polytetrafluoroethylene) membrane, the inner wall of the branches is smooth, thereby reducing thrombosis and properly protecting blood vessels in the brain. The main body and the branches are connected without using a suture, so that there is no risk of blood leakage. A proximal fabric is attached on the main body; e.g., a segment of tubular polyester fabric is sewn on the proximal end of the main body, part of region on the proximal end of the polyester fabric is not supported by a metal stent, and the diameter of the polyester fabric in this region is slightly smaller than that of portion of the main body having the metal stent arch, the polyester fabric ensures reliable anastomosis between the stent and the blood vessels, and is also prevented from being crinkled during anastomosis with the blood vessels due to the slightly small diameter of the polyester fabric. In addition, a distal fabric may also be attached on the main body; e.g., a segment of tubular polyester fabric may also be sewn on the proximal end of the main body, a small segment of the region on the distal end of the main body may be not supported by a metal stent, this segment of polyester fabric ensures that the distal end of the main body has a reliable suturing performance, thereby providing guarantee for the long-term surgical treatment.

4) The descending aorta segment of the main body of the aortic arch intraoperative stent in the present invention may be tapered, in order to better adapt to the anatomical shape of the descending aorta segment.

5) One circle of the circular waveform stent on the topmost end of the branches of the aortic arch intraoperative stent in the present invention adopts a design of densely arranged small waveforms, to ensure that sufficient apposition performance of the top ends of the branches.

6) One circle of the circular waveform stent on the topmost end of the branch of the aortic arch intraoperative stent in the present invention may be necked down (the diameter of the topmost end is the smallest), the other waveforms are straight tube-shaped, in this way, the stability of the branches in the branch vessels of the aortic arch is ensured, and the injury of the branch vessels due to the excessive extension force of the branch to the branch is also avoided.

7) One circle of the circular waveform stent on the bottommost end of each branch of the aortic arch intraoperative stent in the present invention may be necked down (the diameter close to one side of the main body is the smallest), such design may ensure that the branches may freely swing better, in order to better adapt to the anatomical shape differences between the aortic arch and the branch vessels of different patients.

DETAILED DESCRIPTION OF THE PRESENT INVENTION

In order to make the objectives, the technical solutions and the advantages of the present invention more clear, the present invention will be further described in detail with reference to the accompanying drawings and the embodiments. It should be understood that the specific embodiments described here is merely used for explaining the present invention, but not for limiting the present invention.

Figure 1:
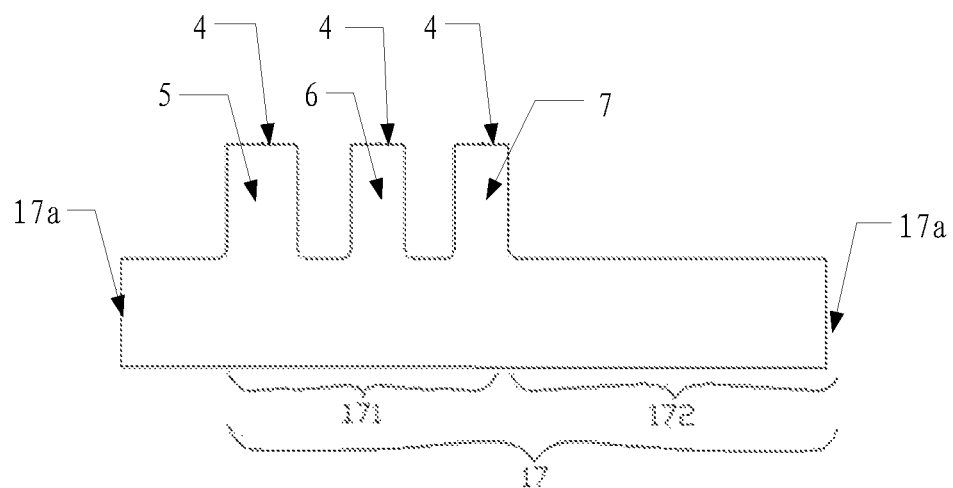
FIG. 1 is a schematic diagram of an aortic arch intraoperative stent provided by the present invention.
Figure 5:
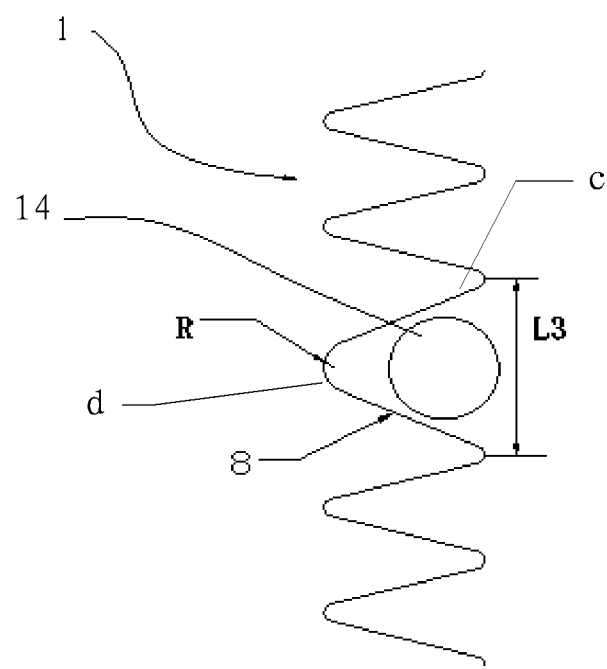
FIG. 5 is a top view of FIG. 3.
Figure 7:
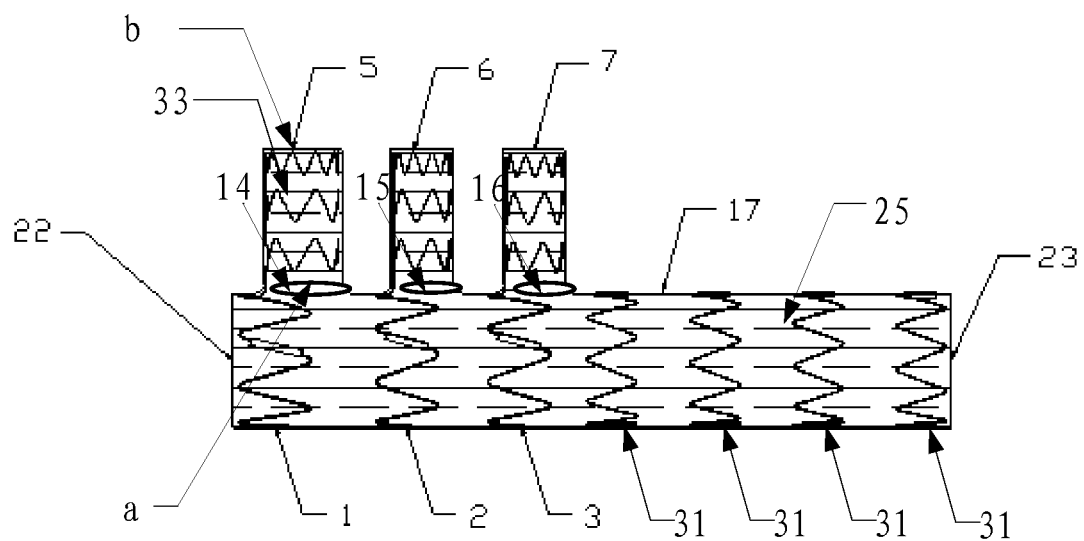
FIG. 7 is a front view of the metal stent of FIG. 3 having been covered with an inner membrane and an outer membrane.

With reference to FIG. 1, FIG. 5 and FIG. 7, the overall structure of an aortic arch intraoperative stent provided by a first embodiment of the present invention is designed to correspond with the shape of the aortic arch, including a main body 17 and at least one branch 5, 6, 7; the aortic arch intraoperative stent is selectively provided with one to three branches according to the involvement of the lesions. The aortic arch intraoperative stent is a covered stent having a membrane: i.e., the main body 17 and the branches 5, 6, 7 are all in a tubular structure which comprises a compressible metal scaffold and a cover membrane 25 on a surface of the metal stent. A first opening 17a is respectively formed on both a proximal end 22 and a distal end 23 of the main body 17. The main body is respectively connected to a first end a of each branch through interfaces 14, 15, 16 at one side with the cover membrane 25, and a second opening 4 is formed on a second end b of each branch opposite to the first end a.

The metal scaffold of the main body 17 and the branches are all formed by a series of axially arranged circular waveform rings, and the arrangement direction of the circular waveform rings on the main body 17 is approximately perpendicular to that of the circular waveform rings on the branches. Each circular waveform ring includes a circular elastic wire formed through an end-to-end connection, and the circular elastic wires are all attached on a tubular wall of the cover membrane 25. Each circular waveform ring has a central axis of symmetry, the elastic wire has several waveforms which are distributed around the central axis of symmetry and are circular through projection along the axial direction, and wave-like through projection along the radial direction. Being circular through projection along the axial direction refers to the projection of the elastic wire along the axis of the circular waveform ring, and being wave-like through projection along the radial direction refers to the projection of the elastic wire along the radial direction of the circular waveform ring. The several circular waveform rings are divided into several first circular waveform rings 31, second circular waveform rings (1, 2, 3) with the same number as the interfaces (14, 15, 16), and several third circular waveform rings 33 located at each branch and spaced-apart along the extension direction of the branch. The several first circular waveform rings 31 are adjacent to each other and spaced-apart along the extension direction of the main body to function as first components distributed on a descending aorta segment 172 of the main body, and all the second circular waveform rings 1, 2, 3 are adjacent to each other and spaced-apart along the extension direction of the main body to function as second components distributed on an arch segment 171 of the main body 17.

The main body 17 includes the arch segment 171 and the descending aorta segment 172 which are smoothly connected into a whole body through the cover membrane 25; the arch segment 171 is to be deployed to a position where the aortic arch is located, and the descending aorta segment 172 is to be deployed inside the aortic arch. The proximal end 22 of the main body 17 is located at the arch segment 171 and close to the heart, and the distal end 23 of the main body 17 is located at the descending aorta segment 172 and far from the heart. The branches (5, 6, 7), and the interfaces (14, 15, 16) all correspond to the second circular waveform rings (1, 2, 3), respectively. An approximately circular closed dividing line c is located at each interface on the cover membrane 25, a segment of the waveform 8 on the second circular waveform ring corresponding to the interface is the closest to the closed dividing line c of the interface, and forms a V-shaped dividing line d on the cover membrane 25. The closed dividing line c is embedded in a region enclosed by the V-shaped dividing line d. An opening width L3 of the V-shaped dividing line d may be greater than a maximum outer diameter of the closed dividing line c, so that at least half of the area within the closed dividing line c is located in the region enclosed by the V-shaped dividing line d. The opening width L3 of the V-shaped dividing line d may also be equal to or slightly smaller than the maximum outer diameter of the closed dividing line c, and a small part of the area within the closed dividing line c may be in the region enclosed by the V-shaped dividing line d. As a more common implementation, at least one second circular waveform ring is located in a position below each branch corresponding to the main body 17, and at least one second circular waveform ring has one waveform 8 thereon bypassing near the edge of the interface formed by the first end a of the corresponding branch, FIG. 5 is a local top view of the main body 17, in order to clearly show the relative position between the interface 14 on the cover membrane and the second circular waveform ring 1 in one of the embodiments; the cover membrane is omitted from the figure, as a matter of fact, the second circular waveform ring 1 and the interface 14 are both located on the tubular wall where the cover membrane of the main body 17 is located.

Still as shown in FIG. 5, at least one part of a projection line (i.e. closed dividing line c) of the intersecting line of the second circular waveform ring 1 corresponding to one branch 5 closest to the proximal end is embedded in the projection line region of the waveform 8 projected in the same direction and the waveform 8 encircles the intersecting line; herein, a relative axial height between the proximal end of the projection line region 8 and the proximal end of the projection line c is 2 to 8 mm, preferably as small as possible. In general, the waveform which encircles the intersecting line may be a waveform with a minimum wave height in the second circular waveform ring 1.

Figure 2:
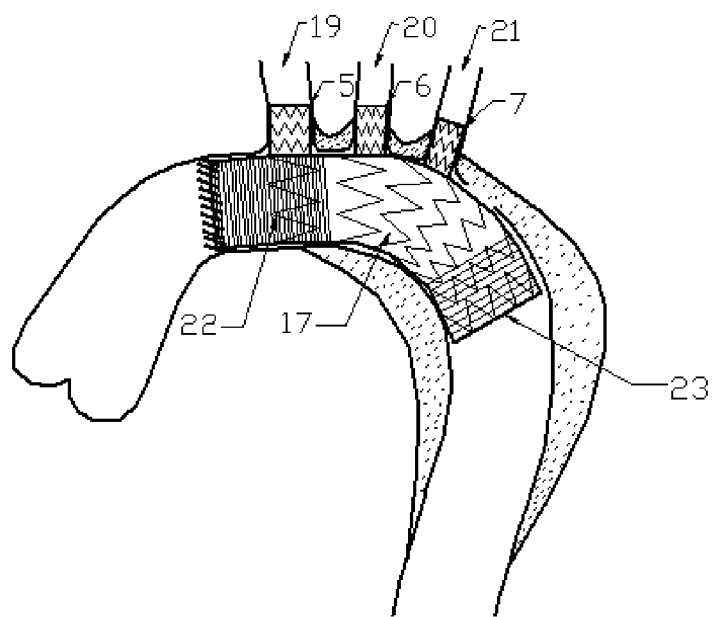
FIG. 2 is illustrates the aortic arch intraoperative stent of FIG. 1 after implantation in the aortic arch.

In the embodiment, the aortic arch intraoperative stent includes a main body 17 and a first branch 5, a second branch 6 and a third branch 7; the main body 17 and the three branches are all in tubular structure which includes a metal scaffold and a cover membrane 25 covering the metal scaffold; and in the free state, the axial direction of the first branch 5, the second branch 6 or the third branch 7 is perpendicular to that of the main body. With reference to FIG. 2 which is a schematic diagram of the aortic arch intraoperative stent having been deployed in the aortic arch, wherein the main body 17 corresponds to the human aortic arch and the first branch 5, the second branch 6 and the third branch 7, respectively, corresponds to three branch vessels which are the innominate artery 19, the left common carotid artery 20 and the left subclavian artery 21 on the aortic arch. The diameters of the main body 17 and the first branch 5, the second branch 6 and the third branch 7 are respectively matched with the inner diameters of the corresponding vessels, e.g., the diameter of the proximal end 22 of the main body 17 is 32 mm, the diameter of the distal end 23 thereof is 32 mm; the first branch 5, the second branch 6 and the third branch 7 are all straight tube-shaped, and the diameters thereof are respectively 18 mm, 14 mm and 14 mm.

Figure 3:
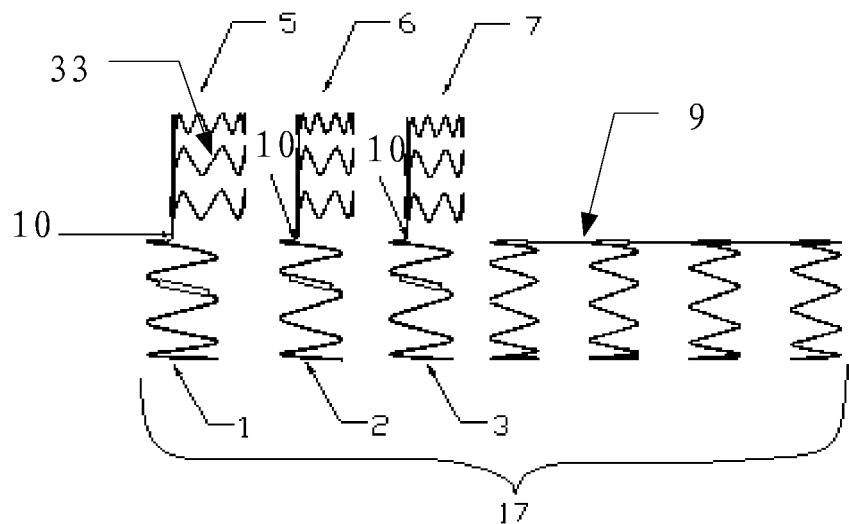
FIG. 3 is a front view of a metal stent applied to an aortic arch intraoperative stent provided by a first embodiment of the present invention.
Figure 8:
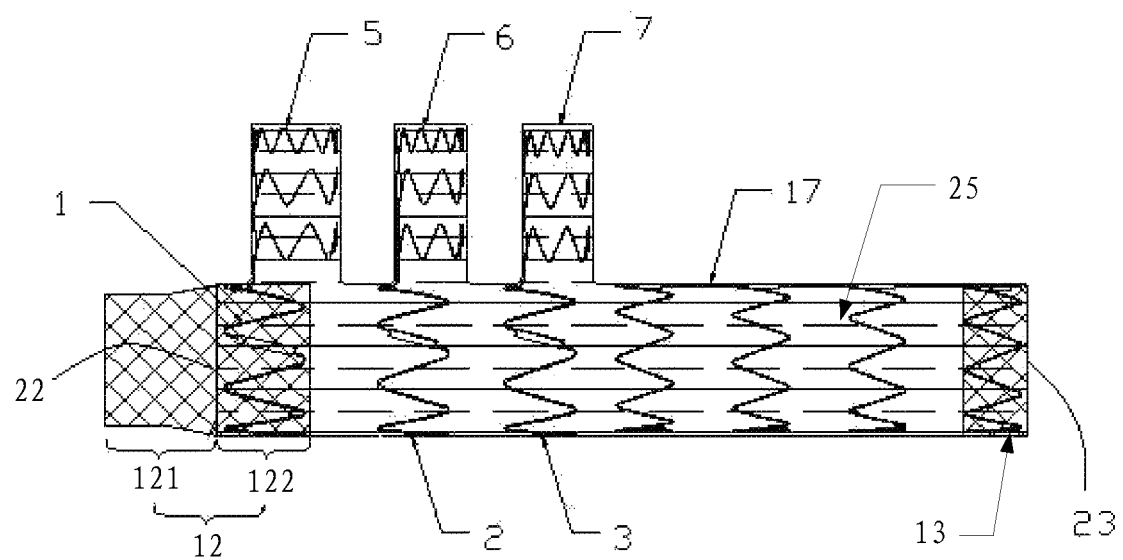
FIG. 8 is a front view of the aortic arch intraoperative stent provided by the first embodiment of the present invention, showing a first way for arranging a polyester fabric on a distal end.

In order to clearly illustrate the metal scaffold portion of the aortic arch intraoperative stent, the cover membrane is not shown in some of the figures. With reference to FIG. 1, FIG. 3 and FIG. 8, the metal scaffolds on the main body 17 and the three branches are respectively formed by spaced-apart circular waveform rings with equal diameter in the axial direction, and the circular waveform rings are formed by braiding elastic nickel-titanium alloy wire with a diameter of 0.55 mm; the third circular waveform rings 33 on the first branch 5, the second branch 6 and the third branch 7 are formed by braiding nickel-titanium alloy wire with a diameter of 0.4 mm. The main body 17 includes the arch segment 171 and the descending aorta segment 172 connected to the arch segment 171, and the arch segment 171 includes three second circular waveform rings 1, 2, 3 respectively for supporting the first branch 5, the second branch 6 and the third branch 7, The three first circular waveform rings 1, 2, 3 are independent of each other, and respectively located below the first ends a of the first branch 5, the second branch 6 and the third branch 7. Preferably, in order to ensure that the adjustable distance between the three branches the three second circular waveform rings 1, 2, 3 are not connected together by a connection rod but closely attached on the same cover membrane 25 to form an integrated body; in this way, the branches may automatically adjust the relative position according to the distance between the branches vessels. Herein, the distance between the adjacent two second circular waveform rings is 2 to 8 mm; here, the so-called shortest distance for example is a distance between a wave trough of a certain second circular waveform ring and a wave peak of an adjacent second circular waveform ring at the distal side. Similarly, in order to ensure that the relative position between the branches may be automatically adjusted better, the third circular waveform rings between the two adjacent branches are also not connected by a rigid connecting piece (i.e. connected by the connection rod).

The descending aorta segment 172 of the main body 17 is close to the distal end 23, and the first circular waveform rings 31 of the descending aorta segment 172 are connected together through first connection rods 9 which are linear elastic wires. Each of the metal scaffolds of the first branch 5, the second branch 6 and the third branch 7 comprises three circular waveform rings connected together through the connection rod, and respectively form a one-to-one connection with the second circular waveform ring 1, the second circular waveform ring 2 or the second circular waveform ring 3 on the main body 17 through second connection rods 10 which are L-shaped elastic wires. Each branch may also be connected to the plurality of third circular waveform rings 33 on the branch through a long arm of the second connection rod 10, and then connected to a corresponding second circular waveform ring on the main body through a short arm of the second connection rod 10. In this way, the supporting performance for the branches provided by the main body 17 may be further improved; the second connection rods 10 may be arranged on one side of the proximal end 22 on the branch facing to the main body 17, so it can be compressed to deflect toward the distal end 23 of the main body 17, and may also ensure that the branch is restored to a position which is approximately perpendicular to the main body 17, thereby avoiding the risk that the branch will not be restored to the normal position which may be caused by excessive inclination to the distal end 23.

In order to enable an included angle between the branch and the main body 17 to appropriately change to adapt to the blood vessel profiles of different patients, preferably, for any branch, a distance L4 between the third circular waveform ring 33 thereof close to its first end a and the main body 17 is in the range of 4 mm to 10 mm; i.e., the minimum distance L4 between the metal ring at the bottom end of each branch and the main body is 4 to 10 mm, according to this, the length of the second connection rod 10 is chosen. Usually, the supporting capability required by the third branch 7 is greater than that required by the first branch 5 and the second branch 6, the second connection rod 10 of the third branch 7 may be made of thicker or harder material, while the second connection rods 10 of the first branch 5 and the second branch 6 may be made of slightly slender or slightly soft material.

Preferably, the second circular waveform ring 1 is closer to the proximal end 22 of the main body 17 than the first branch 5, and the second connection rod 10 of the first branch 5 is arranged on one side close to the proximal end 22 of the main body 17, which is beneficial to positioning the first branch 5 in the branch vessel. In order to enable the support for the branches provided by the main body to be performed uniformly, preferably, the second circular waveform ring 2 is closer to the first branch 5 than the second branch 6, and the second circular waveform ring 3 is closer to the second branch 6 than the third branch 7.

Figure 4:
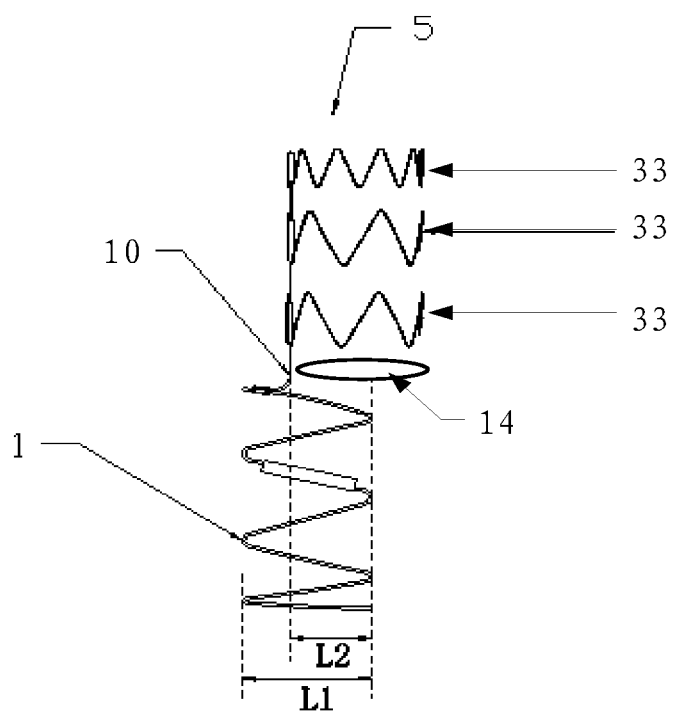
FIG. 4 is a front view of a branch and a second circular waveform ring corresponding to the branch applied to the aortic arch intraoperative stent of FIG. 3.

In order to enhance the apposition performance of the branches, for the third circular waveform rings 33 of each branch, the third circular waveform ring 33 close to the second end b of this branch has the smallest wave height and the largest wave number, i.e., the arrangement of the waveforms of the third circular waveform ring 33 on the top of the branch is more dense; taking the first branch 5 as an example, with reference to FIG. 4, there are nine waveforms of the first circle of the third circular waveform ring 33 located on the top end, and there are six waveforms of the other two circles of the third circular waveform rings 33 respectively.

The bottom of the cover membrane 25 of each branch is connected to the cover membrane 25 on the side wall of the main body 17 to form an interface (14, 15, 16) on the cover membrane 25 of the main body 17, and a lumen of the main body 17 is communicated with the branch through the interface. With reference to FIG. 5 which is a top view of the first branch 5, one waveform 8 of the second circular waveform ring 1 just bypasses a circular interface 14 on the cover membrane 25 of the main body 17, and the cover membrane 25 on the side wall of the main body 17 and the cover membrane 25 of the first branch 5 are encircling the interface 14 and connected together into an integration; in other words, the interface 14 is located on the side wall of the main body 17 and also located on the first end a of the first branch 5. As the cover membrane 25 has a certain thickness and toughness, the pressure to the main body 17 from the first branch 5 is transferred to the waveforms 8 on the second circular waveform ring 1 through the cover membranes 25 surrounding the interface 14; that is to say, the second circular waveform ring 1 provides a support for the first branch 5. With reference to FIG. 5, in order to improve the supporting capability of the second circular waveform ring 1 to the first branch 5, the ratio of the embedded depth of the closed dividing line c embedded in the region enclosed by the V-shaped dividing line d to the height of the region enclosed by the V-shaped dividing line d is at least 50%; or, with reference to FIG. 4, the embedded depth L2 of the interface 14 entering the region encircled by the waveforms 8 of the second circular waveform ring 1 is greater than 50% of the height L1 of the waveforms 8. In this way, the radial support for the branches by the main body 17 may be improved, so that the branches may be safely pushed into the corresponding branch vessels by the main body 17 having been deployed, and the deployed branches may be prevented from slipping out of the corresponding branch vessels.

Preferably, with reference to FIG. 4, the height L1 of the waveforms 8 of the second circular waveform ring 1 is greater than a radius of the circular interface 14, and a center of the interface 14 is also located in the region encircled by the waveforms 8. Preferably, the relative position between the second circular waveform ring 2 and the second branch 6 meets the same condition, and the relative position between the second circular waveform ring 3 and the third branch 7 also meets the same condition, so as to improve the radial support for each branch. With reference to FIG. 5, for the second circular waveform ring 1, a fillet radius R of one waveform 8 thereof encircling the interface 14 is 3 mm, and a width L3 of such waveform 8 after being unfolded is 25 mm; a diameter of the interface 14 of the first branch 5 is 18 mm, and then a embedded depth of the interface 14 embedded in the waveform 8 may be up to or more than 50% of the height of the waveform 8. Similarly, the fillet radiuses R of the waveforms 8 of the second circular waveform ring 2 and the second circular waveform ring 3 respectively encircling the corresponding interfaces 15, 16 are both 3 mm, the widths of the two waveforms 8 after being unfolded are both 20 mm, and the diameters of the interfaces 15, 16 of the second branch 6 and the third branch 7 respectively are both 14 mm, Such a design ensures that the waveforms 8 on the main body 17 have enough width to accommodate the interfaces of the corresponding branches, and the embedded depth of the interface embedded in the waveform 8 on the main body 17 may be up to or more than 50% of the height of the waveform 8.

As the formation of the metal scaffolds, a membrane covering process with a covering mandrel 40 begins. The covering mandrel 40, which also comprises a main body and three branches, is matched with the morphological structure of the aortic arch. A membrane covering process includes a first process of manufacturing an inner membrane, the ePTFE membrane is covered on the surface of the mandrel firstly, and the inner membrane may be a single layer of the ePTFE membrane with a thickness of 0.03 to 0.1 mm, or multi-layer of thinner ePTFE membranes superimposed to the equal thickness to complete the inner membrane process.

Figure 6:
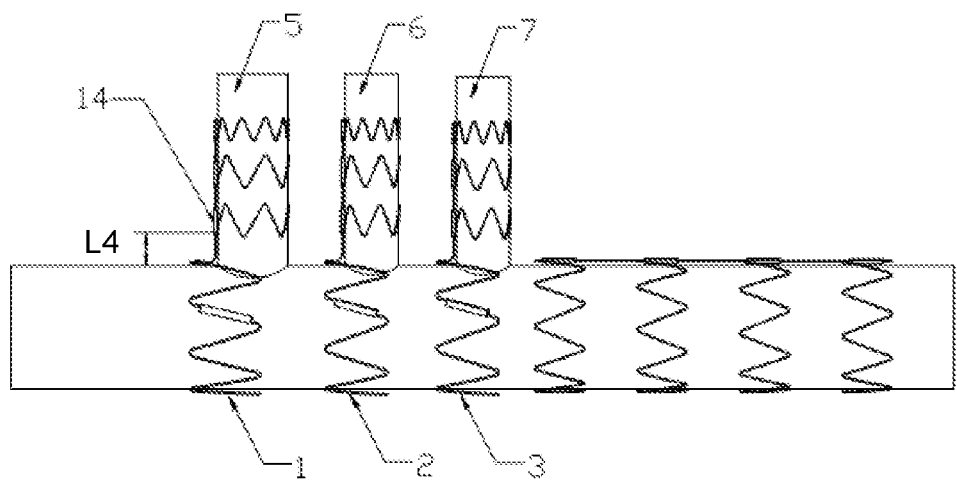
FIG. 6 is a front view of the metal stent of FIG. 3 having been covered with an inner membrane.

A second process is a process of sleeving the braided metal scaffolds on the surface of the mandrel covered with the inner membrane. Specifically, with reference to FIG. 6, the second circular waveform ring 1 and the metal scaffolds on the first branch 5, the second circular waveform ring 2 and the metal scaffolds on the second branch 6, the second circular waveform ring 3 and the metal scaffolds on the third branch 7, and other circular waveform rings on the main body 17 close to the distal end 23, are respectively placed in the positions as shown in FIG. 6. Preferably, the embedded depth of each branch of the mandrel embedded in the waveform 8 of the second circular waveform ring may be up to or more than 50% of the height of the waveform 8.

A third process is a process of making an outer membrane, and the ePTFE membrane is further covered on the surface of the mandrel to fully cover the entire scaffold (including the metal scaffolds of the main body 17 and the three branches). The outer membrane may be a single layer of the ePTFE membrane with a thickness of 0.03 to 0.1 mm, or multi-layer of thinner ePTFE membranes superimposed to the equal thickness. In a region in which the inner membrane and the outer membrane are directly attached to each other, the total thickness of the cover membrane 25 is 0.06 to 0.2 mm, After the completion of the three processes, the inner and outer ePTFE cover membranes are attached together through a method of applying pressure in high temperature, and the metal scaffolds are fixed in the middle of the cover membranes 25. After the completion of this process, the whole stent is disassembled from the mandrel, the redundant ePTFE membranes on the two ends of the main body 17 are cut off to form the proximal end 22 and the distal end 23, finally as shown in FIG. 7. Preferably, a distance from the proximal end 22 of the cover membrane 25 on the main body 17 to the first end a of the first branch 5 is 5 to 10 mm.

After the ePTFE membrane has been covered, there are optionally steps of suturing a proximal fabric 12 or a distal fabric 13 on the main body 17, the two may be polyester fabric or Dacron. With reference to FIG. 8, in order to facilitate suturing of the proximal end 22 of the main body 17 of the aortic arch intraoperative stent to the blood vessels, after the completion of membrane covering, a tubular polyester fabric that is the proximal fabric 12 is sutured on the proximal end 22 of the main body 17; a fixed end of the polyester fabric and the second circular waveform ring 1 close to the proximal end 22 are sutured together, and a distance from a free end of the polyester fabric to the first branch 5 is 25 to 35 mm, preferably 30 m. The proximal fabric 12 comprises a first segment 121 and a second segment 122, the first segment 121 does not contain any metal scaffold, and there is no metal scaffold for supporting inside the same; the metal ring is used for supporting inside a tube enclosed by the polyester fabric of the second segment 122, and the second segment 122 and the second circular waveform ring 1 may be overlapped and sutured together. The diameter of the tubular polyester fabric in the first segment 121 is 29 mm, which is slightly smaller than that of the main body 17. Since the diameter of the main body 17 in a free state will be slightly greater than that of the blood vessel of the aortic arch, and the diameter of the free end of the polyester tube should be equal to that of the blood vessel, in order to prevent the polyester fabric from being crinkled during suturing of the blood vessel, the diameter of the free end of the polyester tube is slightly smaller than that of the proximal end 22 of the main body 17. And, the diameter of the tubular polyester fabric in the second segment 122 is 32 mm, which is equal to that of the main body 17.

Specifically, the main body 17 is a tubular structure which consists of compressible metal scaffolds and a cover membrane covered on the surface of the metal scaffolds, is compressed into a delivery device and then delivered to the lesion region of the aortic vessel, and restored to the original tubular structure through self-expansion after being deployed and closely apposed to the vessel wall. Therefore, in order to enable the main body 17 to be stably positioned in the blood vessel without slipping out, generally 5% to 20% excess size is designed; i.e., the diameter of the main body 17 is 5% to 20% greater than that of the vessel in the position where the main body is to be deployed, thus the main body 17 is fixed by means of a corresponding restoring force generated by self-expansion thereof in the case of such main body 17 being slightly compressed by the vessel wall.

Figure 9:
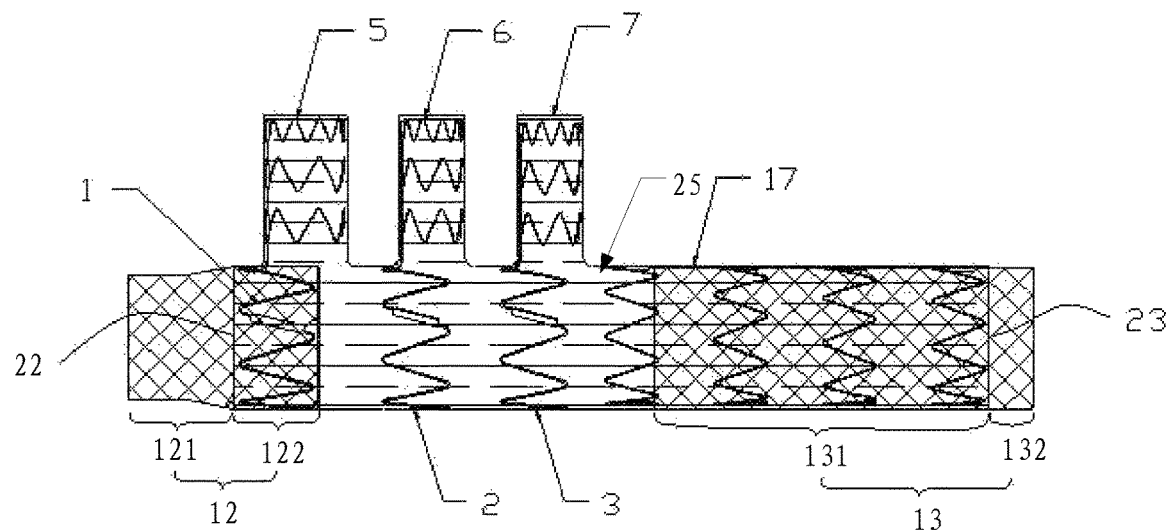
FIG. 9 is a front view of the aortic arch intraoperative stent provided by the first embodiment of the present invention, showing a second manner for arranging the polyester fabric on the distal end.
Figure 9A:
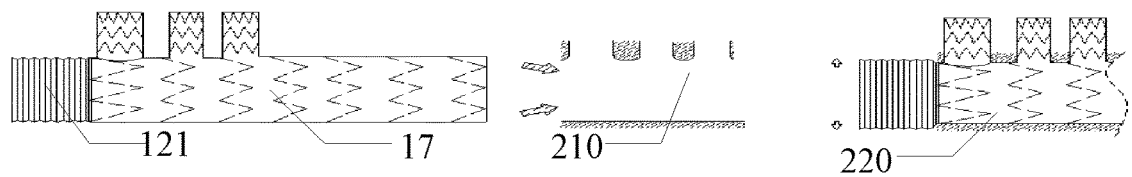
FIG. 9a is a schematic diagram when a diameter of a first segment of a proximal fabric in the first embodiment of the present invention is equal to that of a main body.
Figure 9B:
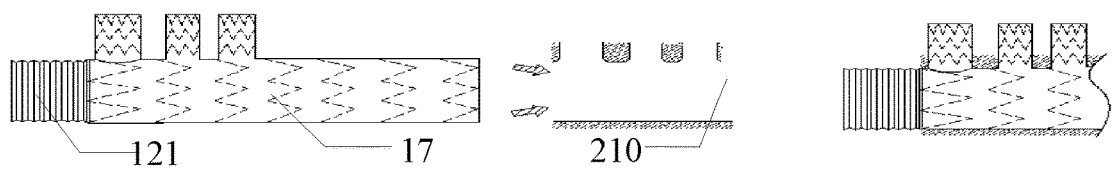
FIG. 9b is a schematic diagram when the diameter of the first segment of the proximal fabric in the first embodiment of the present invention is slightly smaller than that of the main body.

However, the first segment 121 adjacent to the proximal end of the main body 17 is a non-elastic polyester fabric, and is fixed to the blood vessel by suturing during surgery; therefore, it assumes that when the diameter of the proximal end of the main body 17 is equal to that of the first segment 121, with reference to FIG. 9a, after the aortic arch intraoperative stent is implanted in the aortic vessel 210, the compressed main body 17 is closely apposed to the vessel wall; meanwhile, as the diameter of the first segment 121 is slightly greater than that of the blood vessel, on the one hand, the first segment 121 cannot be closely apposed to the vessel wall to form crinkles, thus resulting in the subsequent formation of thrombosis; on the other hand, a step structure 220, which will affect the hemodynamics, is formed at a junction of the compressed main body 17 and the first segment 121 due to the diameter difference thereof at this location, thus also resulting in the subsequent formation of thrombosis. As a result, with reference to FIG. 9b, the diameter of the first segment 121 is set to be slightly smaller than that of the proximal end of the main body 17; e.g., the diameter of the first segment 121 is correspondingly reduced according to the excess size of the main body 17; after the aortic arch intraoperative stent is implanted in the aortic vessel 210, the diameter of the compressed main body 17 is mostly equal to that of the first segment 121, thus eliminating the step structure to effectively reduce the risk of the subsequent formation of thrombosis caused by the same.

Figure 9C:
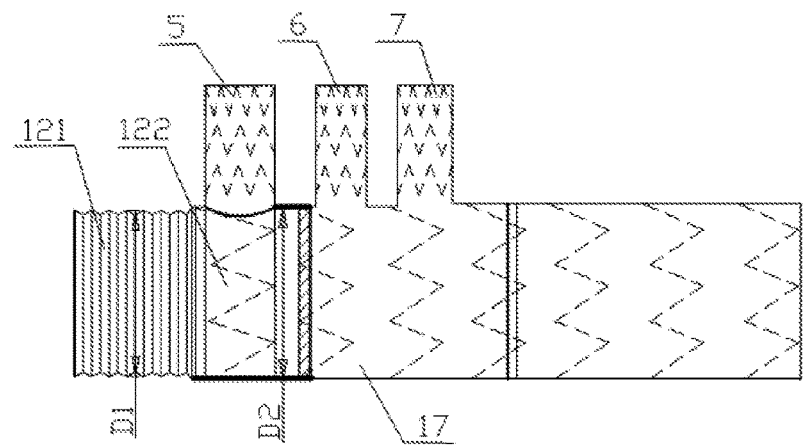
FIG. 9c is a schematic diagram when the proximal fabric in the first embodiment of the present invention is rib polyester fabric.

The proximal fabric 12 may be a plain weave polyester fabric or ribbed polyester fabric; during the suturing process of the first segment 121 of the proximal fabric 12 to the vessel wall, the plain weave polyester fabric may not maintain a solid structure during the suturing process, and is easy to be collapsed, so that it is not convenient for doctors to carry out the suturing operation. However, the ribbed polyester fabric during use always maintains a tubular structure and a rib folding structure, so that it is convenient for doctors to insert a needle to speed up the suturing and reduce the operation time. FIG. 9c shows a case where the first segment 121 and the second segment 122 are both ribbed polyester fabric.

Figure 9D:
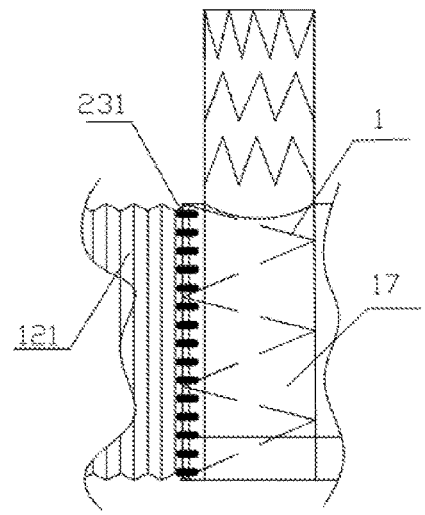
FIG. 9d is a schematic diagram showing the suturing of the rib polyester fabric in FIG. 9c and the main body.

The distal end of the second segment 122 may be deployed between two adjacent branch vessels or deployed on the distal side of the branch vessel 7, so that at least one branch vessel passes through the second segment 122 along the radial direction. For example, with reference to FIG. 9c, the distal end of the second segment 122 is deployed between the branch vessels 5 and 6, and the branch vessel 5 passes through the second segment 122 along the radial direction. FIG. 9d shows a suturing structure 231 of the first segment 121 to the main body 17, the suturing structure 231 closely sutures the first segment 121 and the main body 17 through a method of axial suturing with an axial stitch, having the advantage that the transition position may be smooth inside and outside to avoid forming a gap between the main body 17 and the short fabric 12.

Figure 9E:
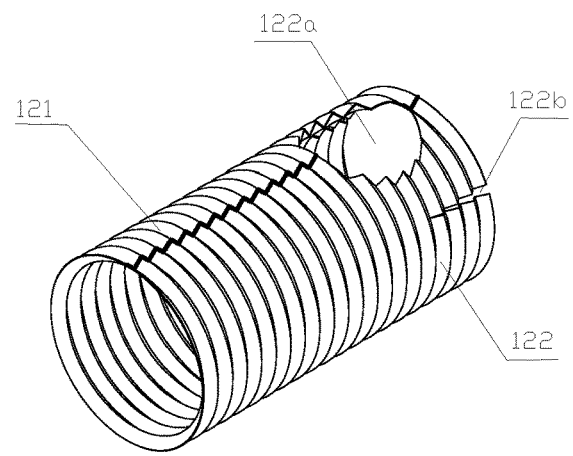
FIG. 9e is a schematic diagram showing the preparation of the proximal fabric from the rib polyester fabric in FIG. 9c.

With reference to FIG. 9e, during the manufacturing process, a hole 122a may be formed on the polyester fabric of the second segment 122 firstly, with a pore diameter thereof being slightly greater than the diameter of the branch vessel passed through; i.e., the difference between the two may be about 0.2 mm, which may be set according to the specific circumstances. By setting this structure, the second segment 122 may be sutured on the main body 17 more firmly, so that the whole proximal fabric does not easily slip out of the main body 17. Similarly, in order to avoid forming the step structure, the diameter D2 of the second segment 122 is mostly equal to that of the main body 17, and is slightly greater than that of D1 of the first segment 121, Since the diameter D2 of the second segment 122 is slightly greater than that of D1 of the first segment 121, the proximal fabric 12 may be manufactured by an integrated artificial vascular stent (not shown) with large diameter on one end and small diameter on another end during manufacturing; or when a cylindrical artificial vascular stent with uniformly-distributed diameter is selected, in order to facilitate sleeving the second segment 122 into the proximal end of the main body 17, at least one incision 122b may be formed on the distal end of the second segment 122 by scissoring (e.g., forming 1 to 3 incisions distributed along the circumferential direction), and the axial length of the incision 122b is approximate to the height of the second circular waveform ring of the most distal end covered by the second segment 122. Afterwards, the polyester fabric sleeved on the second circular waveform ring is pulled to be smooth, in order to facilitate suturing.

Figure 9G:
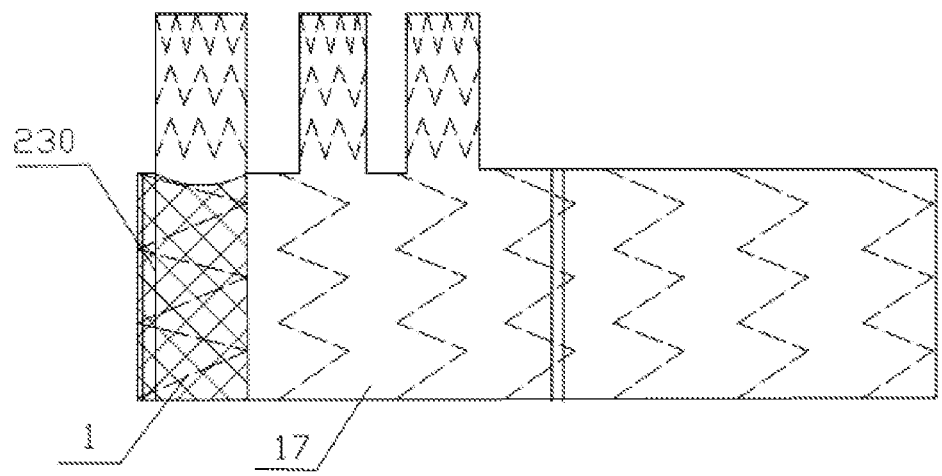
FIG. 9g is a schematic diagram of the proximal fabric in the first embodiment of the present invention including a second layer of proximal fabric.

The proximal fabric may further be a multilayer structure including a first layer of proximal fabric and a second layer of proximal fabric, and the first layer of proximal fabric includes the first segment 121 and the second segment 122. With reference to FIG. 9g, the second layer of proximal fabric 230 is closely apposed to the inner wall the PTFE membrane) at the proximal end of the main body 17 to cover part or the whole of the second circular waveform ring 1; e.g., the second layer of proximal fabric 230 may be fixed on the main body 17 by suturing. The second layer of proximal fabric 230 may be plain weaving polyester fabric which may avoid crinkles forming inside the lumen of the main body 17 and reduce the risk of thrombosis in the future, compared with the ribbed polyester fabric. The proximal end of the second layer of proximal fabric 230 extends out from the incision at the proximal end of the main body 17, and then fixed to the main body 17 by suturing after being folded to the distal end from outside of the lumen of the main body 17, which is overturned and sutured for a circle along the proximal opening of the main body 17. By adopting the outward overturn and fixing structure, on the one hand, the proximal end of the second layer of proximal fabric 230 may be retained in a constrained state, thereby preventing 'swinging' in the blood; on the other hand, the blood may be prevented from entering a gap between the PTFE membrane and the second layer of proximal fabric 230 of the stent, so that the 'outward overturn' may reduce the risk of subsequent formation of thrombosis.

Figure 9H:
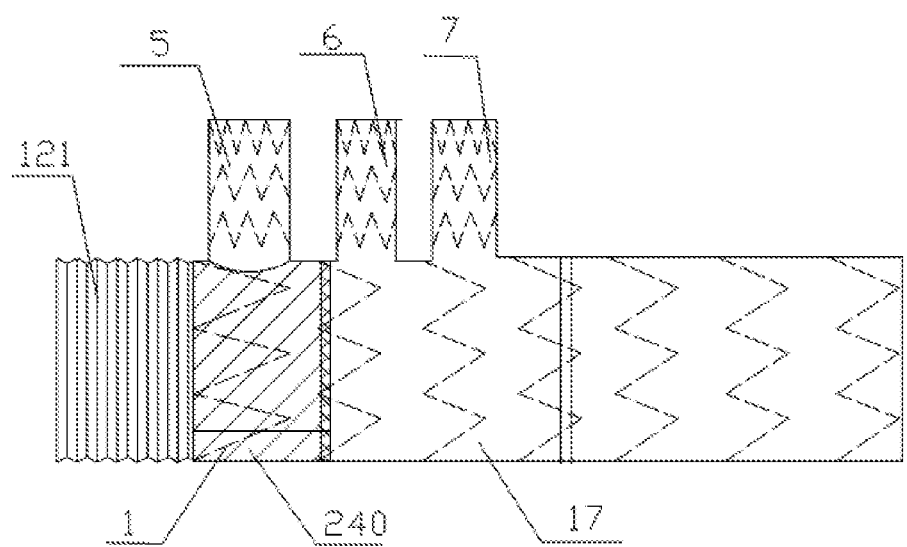
FIG. 9h is a schematic diagram of the proximal fabric in the first embodiment of the present invention including a third layer of proximal fabric.

The proximal fabric with a multi-layer structure may include the second layer of proximal fabric 230 and a third layer of proximal fabric 240; with reference to FIG. 9h, the third layer of proximal fabric 240 is covered on the main body 17 from the outermost layer, and fixed on the main body 17. The proximal end of the third layer of proximal fabric 240 may be aligned with a proximal end face of the main body 17, and the distal end thereof is deployed between the branch 5 and 6, or aligned with the distal end of the second segment 122 (not shown), so that the second segment 122 is fully covered, thereby avoiding direct contact between the second segment 122 made of the ribbed polyester fabric and the vessel wall. The third layer of proximal fabric 240 may be a plain weaving polyester fabric, so that the transition between the first segment 121 and the main body 17 is smoother to improve the apposition between the entire stent and the aorta, thereby improving the long-term stability of the stent. In addition, in the clamping process of hemostatic forceps, the hemostatic forceps directly contact and clamp the third layer of proximal fabric 240 to avoid direct contact with the second circular waveform ring 1, which may enhance the clamping effect and may also protect the hemostatic forceps.

Figure 9I:
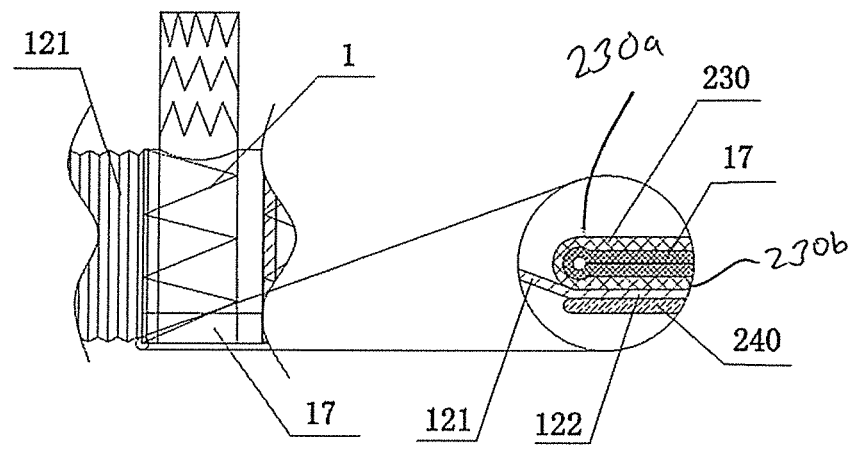
FIG. 9i is a schematic diagram of the proximal fabric in the first embodiment of the present invention including the first, second and third layers of the proximal fabric.

With reference to FIG. 9i, in an embodiment of the present invention, the proximal fabric includes the second layer of proximal fabric 230, the first layer of proximal fabric and the third layer of proximal fabric 240 in sequence from the inside to the outside, wherein the first layer of proximal fabric includes the first segment 121 and the second segment 122. The second layer of proximal fabric 230 has an inner segment 230a and a folded segment 230b. FIG. 9i further shows a section enlarged drawing of the proximal end face of the main body 17, the second layer of proximal fabric 230 is apposed to the inner wall of the main body 17, and overturned from the proximal edge of the main body 17 to cover the proximal edge of the main body 17 (i.e., the PTFE membrane of the main body 17); the first segment 121 together with the second segment 122 are attached and covered on the second layer of proximal fabric 230 and a part of the main body 17 from the outside; the third layer of proximal fabric 240 is attached and covered on the second segment 122 from the outermost layer, or on the second segment 122 and a part of the main body 17, to form the multi-layer structure of the proximal fabric.

In addition, the distal end 23 of the main body 17 is sutured with a distal fabric 13. FIG. 8 shows a first arrangement for the polyester fabric of the distal fabric 13 on the distal end 23. The polyester fabric and the last circle of the first circular waveform ring 31 of the descending aorta segment 172 of the main body 17 are overlapped and sutured together. After the distal fabric 13 is fixed, the distal end 23 of the main body 17 may be ensured to also have a good suturing performance for providing conditions for possible subsequent surgery. If the distal fabric 13 is just aligned with the distal end 23 of the main body 17, the seam for subsequent surgery is sutured together with the distal fabric 13 and the distal end 23 of the main body 17. FIG. 9 shows a second arrangement for the distal fabric 13. The distal fabric 13 sutured on the distal end 23 of the main body 17 may be divided into two regions which are a first region 131 and a second region 132, respectively. The polyester fabric in the first region 131 is overlapped and sutured together with last three circles of the first circular waveform ring 31 on the descending aorta segment 172 of the main body 17; the polyester fabric of the second region 132 has a free end which extends for a distance away from the distal end 23 of the main body 17, and the length of the free end is 8 to 12 mm, preferably 10 mm; the second region 132 does not include a metal scaffold, or is not supported by the first circular waveform ring 31 on the main body 17, After the distal fabric 13 with the free end is fixed, the distal end 23 of the main body 17 may be ensured to also have better suturing performance, and the second region 132 of the distal fabric 13 extends for a distance away from the distal end 23 of the main body 17, so that the seam for subsequent surgery is sutured together with the polyester fabric of the second region 132 of the distal end 23 of the main body 17.

Figure 10:
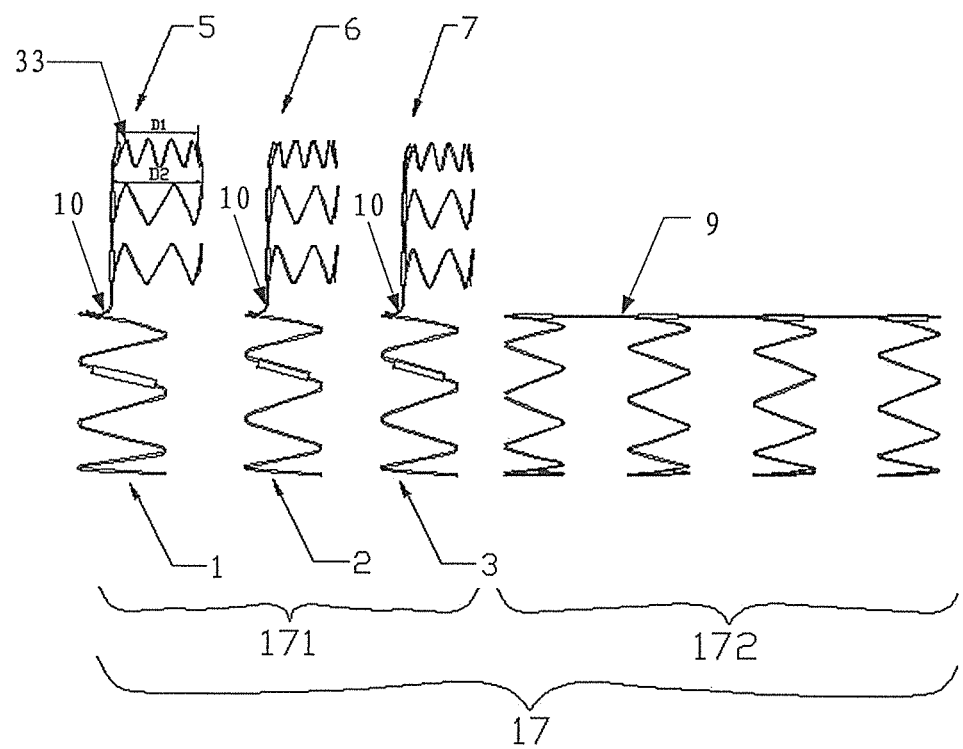
FIG. 10 is a front view of a metal stent applied to an aortic arch intraoperative stent provided by a second embodiment of the present invention.

With reference to FIG. 10, an aortic arch intraoperative stent provided by a second embodiment of the present invention is about the same as that provided by the first embodiment, and differences from the first embodiment are in the following manner; the diameter of one of the circles of the third circular waveform ring 33 closest to the second end b of each branch is gradually decreased along the direction from the first end a to the second end b of the branch, so that the cover membrane at the second end b of the branch has a tapered tube wall which is necked down. For example, the diameter D1 of a circle at an upper end of the third circular waveform ring 33 located on the topmost end of the first branch 5 is 16 mm, the diameter D2 of a circle at a lower end thereof is 18 mm, i.e., the diameter D1 of the upper end is 2 mm smaller than the diameter D2 of the lower end, and other two third circular waveform rings 33, having the diameter of 18 mm, are straight tubular-shaped. The structures of the second branch 6 and the third branch 7 are the same as that of the first branch 5 respectively, with the topmost circle of the third circular waveform ring being tapered and necked down, and the diameter of the upmost end is 2 mm smaller than that of the lower end. Such a design ensures that two circles of the third circular waveform ring 33 on the lower end of each branch are in full contact with the branch vessels and provide sufficient radial support, while the topmost end of one circle of the third circular waveform ring located on the top end will not have very large expansion force for the branch vessels, so as to reduce the injury to the blood vessels.

Figure 11:
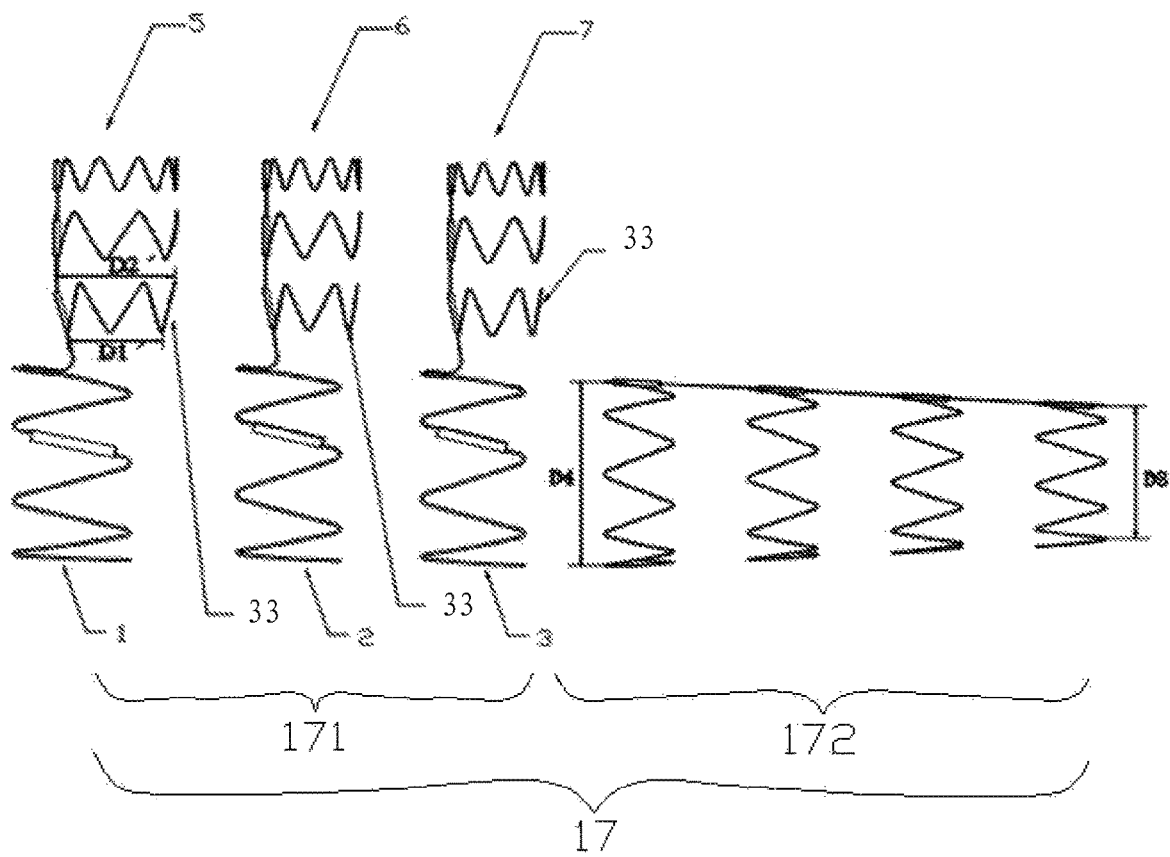
FIG. 11 is a front view of a metal stent applied to the aortic arch intraoperative stent provided by a third embodiment of the present invention.

With reference to FIG. 11, an aortic arch intraoperative stent provided by a third embodiment of the present invention is about the same as that provided by the first embodiment, and difference from the first embodiment are in the following manner: the diameter of the third circular waveform ring 33 which is close to the first end a of one branch is gradually decreased along the direction from the second end b to the first end a of the branch, so that the cover membrane at the first end a of the branch has a tapered tubular wall which is necked down. For example, the diameter D2' of an upper end of the third circular waveform ring 33 located on the bottommost end of the first branch 5 is 18 mm, the diameter D1' of a lower end thereof is 16 mm, i.e., the diameter D2' of the upper end is 2 mm smaller than the diameter D1' of the lower end. The structures of the second branch 6 and the third branch 7 are the same as that of the first branch 5 respectively: the diameters of the third circular waveform ring on the upper end are all 2 mm greater than those thereof on the lower end respectively. Such a design ensures that the three branches may freely swing better during surgery, so as to better adapt to the anatomical shape of different branch vessels on the aortic arch.

Moreover, the diameter of each first circular waveform ring 31 is gradually decreased in the direction from the proximal end 22 to the distal end 23, i.e., the diameter of each first circular waveform ring 31 on the main body 17 is gradually decreased to form a taper integrally; a diameter D4 of the circles first circular waveform ring 31 which is close to the second circular waveform ring 3 is 32 mm, and a diameter D3 of the first circle of the circular waveform ring 31 located on the farthest end is 28 mm: one segment of the main body 17 shaped as the tapered structure is implanted into the descending aorta segment, and the inner diameter of the descending aorta of a human body is also gradually decreased, so that it can better adapt to the anatomical shape of the descending aorta.

It should be understood that as an optimized design of the solution, the diameter of the third circular waveform ring 33 which is close to the second end b of one branch is gradually decreased along the direction from the first end a to the second end b of the branch, so that the second end b of the branch is necked down; the diameter of the third circular waveform ring 33 which is close to the first end a of one branch is gradually decreased along the direction from the second end b to the first end a of the branch, so that the first end a of the branch has a tapered tubular wall which is necked down. In other words, two end portions of the branch may both be designed to be necked down. One third circular waveform ring 33 on the bottommost end of the branch is designed to be necked down, the diameter close to one side of the main body 17 is the smallest; one third circular waveform ring 33 on the topmost end of the branch is designed to be necked down, and the diameter on one side of the topmost end is the smallest.

Figure 12:
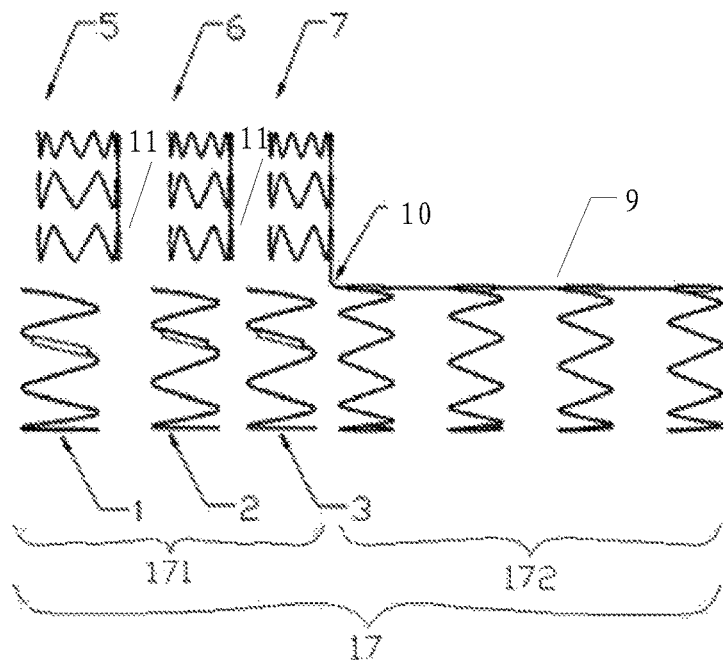
FIG. 12 is a front view of a metal stent applied to the aortic arch intraoperative stent provided by a fourth embodiment of the present invention.

With reference to FIG. 12, an aortic arch intraoperative stent provided by a fourth embodiment of the present invention is nearly the same as that provided by the first embodiment, and the differences from the first embodiment are shown in the following manner: a first connection rod 9, which is a linear elastic wire, is used to connect all the first circular waveform rings 31 together; the aortic arch intraoperative stent further includes a second connection rod 10 which is an L-shaped elastic wire; a short arm of the second connection rod 10 is fixed on the first connection rod 9, and a long arm thereof is connected to all the first circular waveform rings 31 of one branch which is closest to the descending aorta segment 172. In other words, the metal scaffolds of the first branch 5, the second branch 6 and the third branch 7 are respectively connected with the second circular waveform rings 1, 2, 3 of the main body 17, just with the cover membrane 25 but without the connection rod, and there is no connection rod used among the second circular waveform rings 1, 2, 3. Further, the aortic arch intraoperative stent includes third connection rods 11, each of which is provided on one branch which is not connected to the second connection rod 10, and is a linear elastic wire. The bottom of the tubular cover membrane 25 of each branch is fixed on the cover membrane 25 of the main body 17, and these cover membranes 25 are connected continuously to form an integrated body having a certain thickness and toughness. Therefore, the second circular waveform rings 1, 2, 3 can provide a sufficient support for the three branches through the integrated cover membrane 25. Moreover, there is no limitation induced by the connection rod, between the second circular waveform rings 1, 2, 3 and the branches respectively, so that each branch can adjust the angle or distance slightly relative to the main body 17, thus the stent can adapt to the profile and structure of the blood vessels of different patients.

The first waveform rings 31 of the main body 17 are connected together through the connection rods, so as to form the descending aorta segment 172 of the aortic arch intraoperative stent. Due to the fact that the descending aorta segment 172 and the third branch 7 of the aortic arch intraoperative stent must first be released and positioned in the corresponding vessels during surgery, it is most difficult to position the third branch 7 compared to the other two branches: therefore, the metal scaffold of the third branch 7 and the descending aorta segment 172 are connected together through a second connection rod 10, and the second connection rod 10 is an L-shaped elastic wire. A first connection rod 9, which is a linear elastic wire, is used to connect all the first circular waveform rings 31. Preferably, the first connection rod 9 is arranged on one side of the descending aorta segment 172, and such side is close to the branches. The second connection rod 10 may be directly fixed on a first circular waveform ring 31 of the descending aorta segment 172, and it is not necessary for the second connection rod 10 to be connected to the first connection rod 9.

In this embodiment, the second connection rod 10 is located on one side of the third branch 7, and such side is close to the distal end 23 of the aortic arch intraoperative stent, so as to restrain an included angle between the third branch 7 and the descending aorta segment 172; in this way, after deployment, the third branch 7 can point to the direction of a corresponding branch vessel in virtue of the resilience of the second connection rod 10. The second connection rod 10 may also be configured to connect the third circular waveform rings 33 of the third branch 7. Preferably, the second connection rod 10 is extended and fixed on the first connection rod 9 of the descending aorta segment 172 of the aortic arch intraoperative stent, so that the included angle between the descending aorta segment 172 and the third branch 7 is further stabilized, and the third branch 7 is pushed into the branch vessel by virtue of an additional radial support provided by the descending aorta segment 172 of the main body 17. The stable support and positioning between the descending aorta segment 172 and the third branch 7 of the aortic arch intraoperative stent is further beneficial to deployment and positioning of the first branch 5 and the second branch 6, and also allows the first branch 5 and the second branch 6 to adjust the angle and distance according to the blood vessel shape. Optionally, the first connection rod 9 and the second connection rod 10 may be made of the same elastic wire.

An aortic arch intraoperative stent provided by a fifth embodiment of the present invention is nearly the same as that provided by the first embodiment, and the differences from the first embodiment are shown in the following manner: the overall cover membrane in the aortic arch intraoperative stent is made of polyester fabric material or Dacron to replace the ePTFE membrane in the first embodiment; the polyester fabric respectively encircles and covers the outer surface or the inner surface of the metal scaffolds of the main body 17 and of the metal scaffolds of the three branches, and the polyester fabric is sutured together with the metal scaffolds through the seams. Similar to FIG. 9 in the first embodiment, the polyester fabric on the proximal end 22 of the main body 17 has a portion, of which the length is 25 to 35 mm (preferably 30 mm) and the diameter is slightly smaller than those of the other portions of the main body 17, which is not supported by the circular waveform rings; the polyester fabric on the distal end 23 of the main body 17 has a portion which is not supported by the circular waveform rings, of which the length is 8 to 12 mm (preferably 10 mm) and the diameter is equal to that of other portion with the circular waveform rings of the main body 17.

Figure 14:
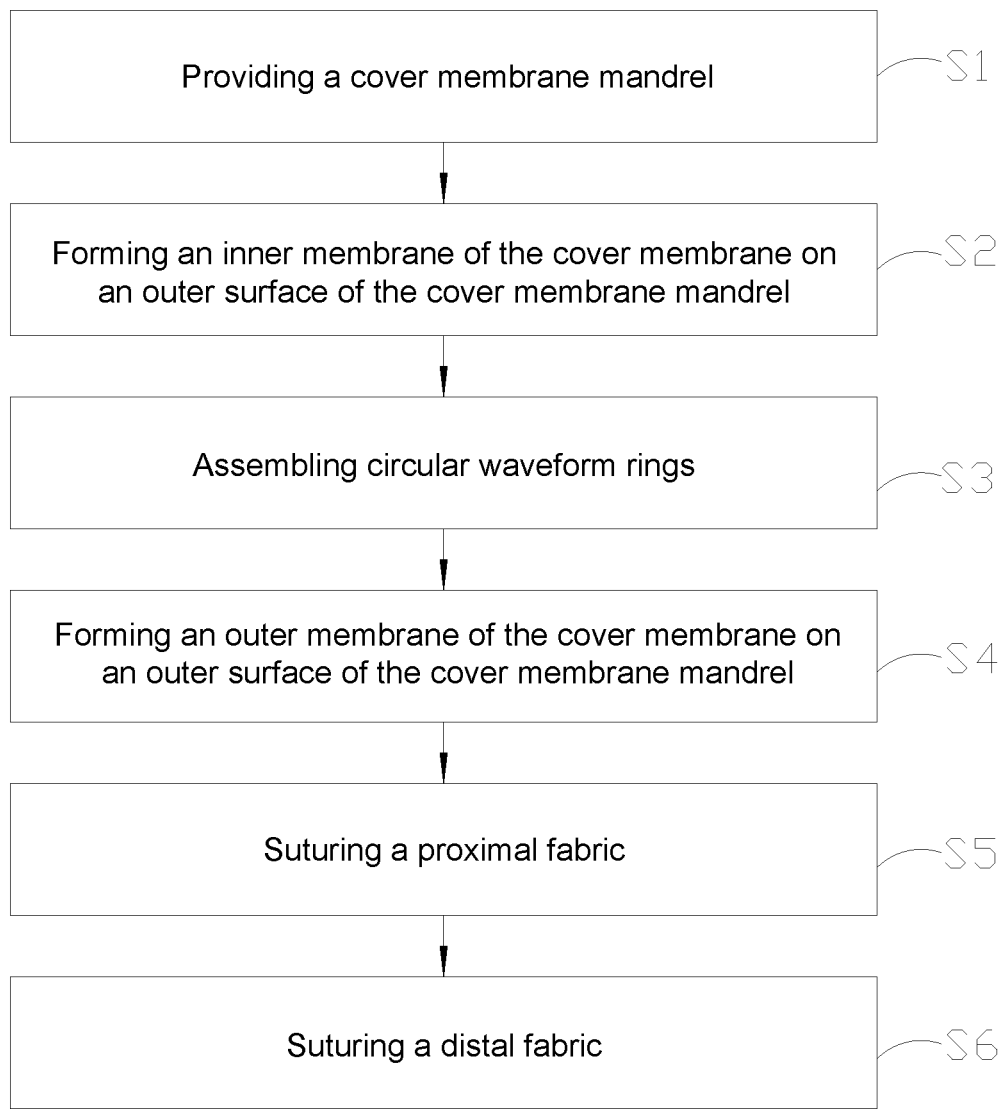
FIG. 14 is a step diagram of a manufacturing method of the aortic arch intraoperative stent provided by the first embodiment of the present invention.

With reference to FIG. 14, a manufacturing method of the aortic arch intraoperative stent provided by the first embodiment of the present invention includes the following steps.

Figure 13:
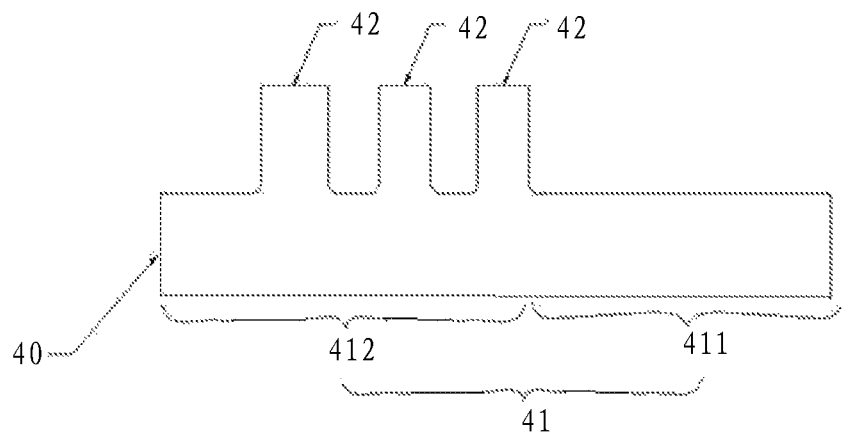
FIG. 13 is a front view of a cover membrane mandrel applied to a manufacturing method of the aortic arch intraoperative stent provided by the embodiment of the present invention.

S1) With reference to FIG. 13, a covering mandrel 40 which is matched with the morphological structure of the aortic arch is provided. The covering mandrel 40 includes a first column 41, and second columns 42 connected to a side wall of the first column 41. The first column 41 comprises a first column segment 411 and a second column segment 412, the number of the second columns 42 is the same as that of the branches of the aortic arch intraoperative stent, and the second columns 42 are connected to the second column segment 412.

S2) An inner membrane of the cover membrane 25 is manufactured on the outer surface of the covering mandrel 40, and the ePTFE membrane is covered on the surface of the mandrel. The inner membrane may be a single layer of the ePTFE membrane with a thickness of 0.03 to 0.1 mm, or multi-layer of thinner ePTFE membranes superimposed to the equal thickness to complete the inner membrane process.

S3) Several circular waveform rings formed by braiding of elastic nickel-titanium alloy wires are provided, wherein the circular waveform rings of the main body 17 are formed by braiding of elastic nickel-titanium alloy wires with a diameter of 0.55 mm, and the third circular waveform rings 33 of the first branch 5, the second branch 6 and the third branch 7 are formed by braiding of nickel-titanium alloy wires with a diameter of 0.4 mm, Several first circular waveform rings 31 are sleeved in spaced-apart manner on the first column segment 411, and each of the second circular waveform rings is sleeved on the second column segment 412 and located adjacent to one side of the second columns 42, wherein such side is close to the proximal end, and such second columns 42 is corresponding to the said second circular waveform ring, and it is required that one waveform 8 of the second circular waveform ring bypasses the corresponding second columns 42. The third circular waveform rings 33 are sleeved in spaced-apart manner on each of the second columns 42, finally as shown in FIG. 6. Preferably, the embedded depth of each branch of the mandrel embedded in the waveform 8 of the main body may be up to or more than 50% of the height of the waveform 8.

S4) An outer membrane of the cover membrane 25 is manufactured on the outer surface of the covering mandrel 40, and the inner membrane and the outer membrane are bonded together and covered on the circular waveform rings. The ePTFE membrane is covered on the surface of the metal scaffolds, so that all the metal scaffolds (including the metal scaffolds of the main body 17 and the three branches) are encased. The outer membrane may be a single layer of the ePTFE membrane with a thickness of 0.03 to 0.1 mm, or multi-layer of thinner ePTFE membranes superimposed to the equal thickness. In a region in which the inner membrane and the outer membrane are directly attached to each other, the total thickness of the cover membrane 25 is 0.06 to 0.2 mm. The inner and outer ePTFE cover membranes are attached together through a method of applying pressure in high temperature, and the metal scaffolds are fixed in the middle of the cover membranes 25. After the completion of this process, the whole stent is disassembled from the mandrel, and the redundant ePTFE membranes on the two ends of the main body 17 are cut off to form a proximal end 22 and a distal end 23, finally as shown in FIG. 7. Preferably, a distance from the proximal end of the cover membrane 25 of the main body 17 to the bottom of the first branch 5 is 5 to 10 mm.

Further, steps S5) and S6) are included, wherein in step 5, a proximal fabric 12 and a distal fabric 13, which are both polyester fabric or Dacron, are sutured on the main body 17. With reference to FIG. 8, a fixed end of the polyester fabric is sutured together with the second circular waveform ring 1 which is close to the proximal end 22, and a distance from a free end of the polyester fabric to the first branch 5 is 25 to 35 mm, preferably 30 mm. The proximal fabric 12 comprises a first segment 121 and a second segment 122, and the second segment 122 is entirely sutured together with the second circular waveform ring 1 adjacent to the proximal end 22. The diameter of the tubular polyester fabric in the first segment 121 is 29 mm, which is slightly smaller than that of the main body 17. And, the diameter of the tubular polyester fabric in the second segment 122 is 32 mm, which is equal to that of the main body 17.

S6) FIG. 8 shows a first way of arranging the polyester fabric on the distal end 23. The polyester fabric is sutured on the distal end 23 of the main body 17, and the distal fabric 13 and the last circle of the first circular waveform ring 31 of the descending aorta segment 172 of the main body 17 are overlapped and sutured together. FIG. 9 shows a second way of arranging the polyester fabric on the distal end 23: the distal fabric 13 sutured on the distal end 23 of the main body 17 comprises two regions which are a first region 131 and a second region 132, respectively. The polyester fabric of the first region 131 is overlapped and sutured together with last three circles of the first circular waveform rings 31 of the descending aorta segment 172 of the main body 17; the polyester fabric of the second region 132 extends out of the distal end 23 of the main body 17 for a distance, of 8 to 12 mm, preferably 10 mm; the second region 132 does not include a metal scaffold, and is not internally supported by the circular waveform ring of the main body 17.

It should be understood that the steps S5) and S6) may be exchanged, and the effect is the same before and after exchange.

Figure 15:
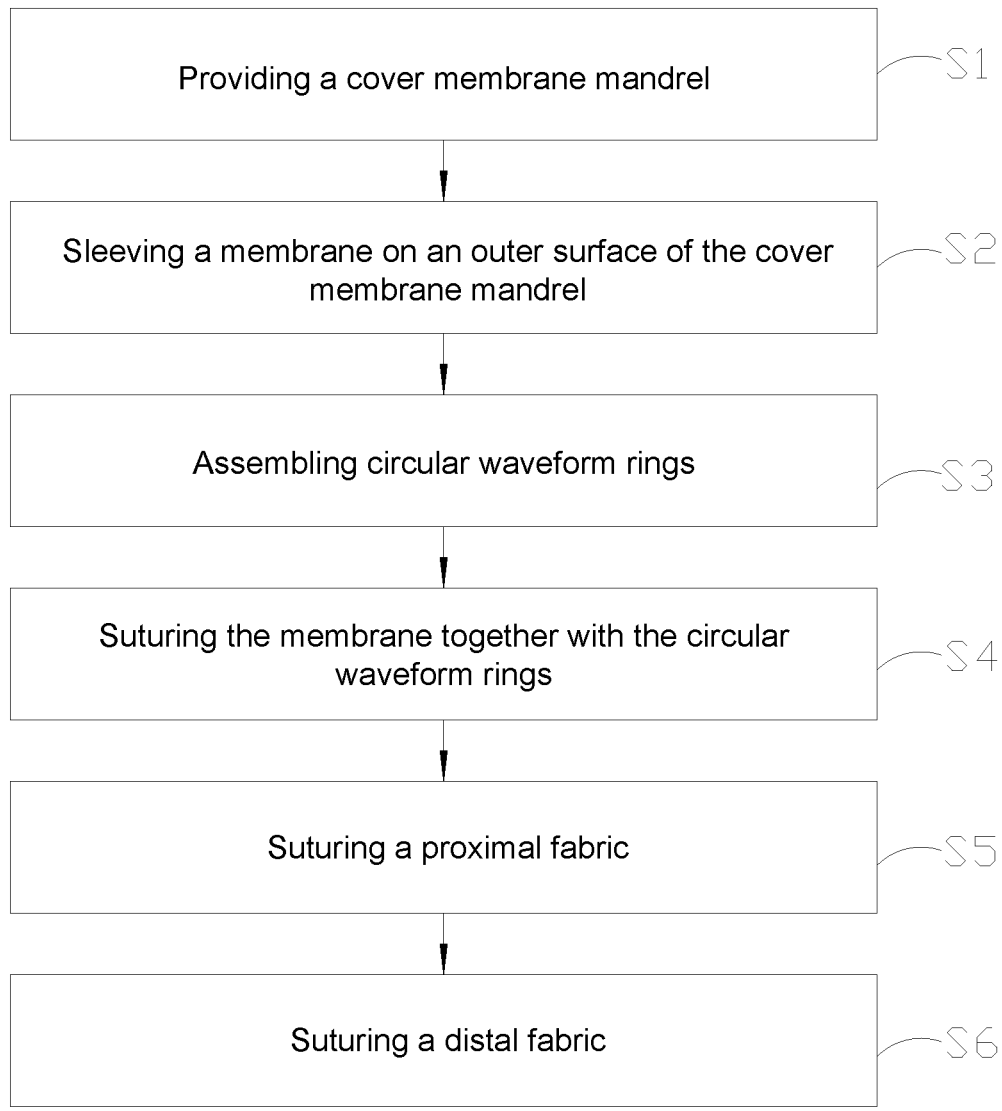
FIG. 15 is a flowchart of a manufacturing method of the aortic arch intraoperative stent provided by the second embodiment of the present invention.

With reference to FIG. 15, a manufacturing method of the aortic arch intraoperative stent provided by a second embodiment of the present invention is nearly the same as that provided by the first embodiment, and the differences from the first embodiment are shown as follows:

Steps S2) and S4):

In step S2), the cover membrane 25, which is polyester fabric or Dacron, is sleeved on the outer surface of the covering mandrel 40.

S4) The cover membrane 25 and the circular waveform rings are sutured together through the seams; the polyester fabric at the proximal end 22 of the main body 17 has a region, of which the length is 25 to 35 mm (preferably 30 mm) and the diameter is slightly smaller than that of the other portion of the main body 17, in such region the polyester fabric is not supported by any circular waveform rings: the polyester fabric at the distal end 23 of the main body 17 has a region which is not supported by any circular waveform rings, such region has a length of 8 to 12 mm (preferably 10 mm) and a diameter which is equal to that of a portion with the circular waveform rings of the main body 17.

Figure 16:
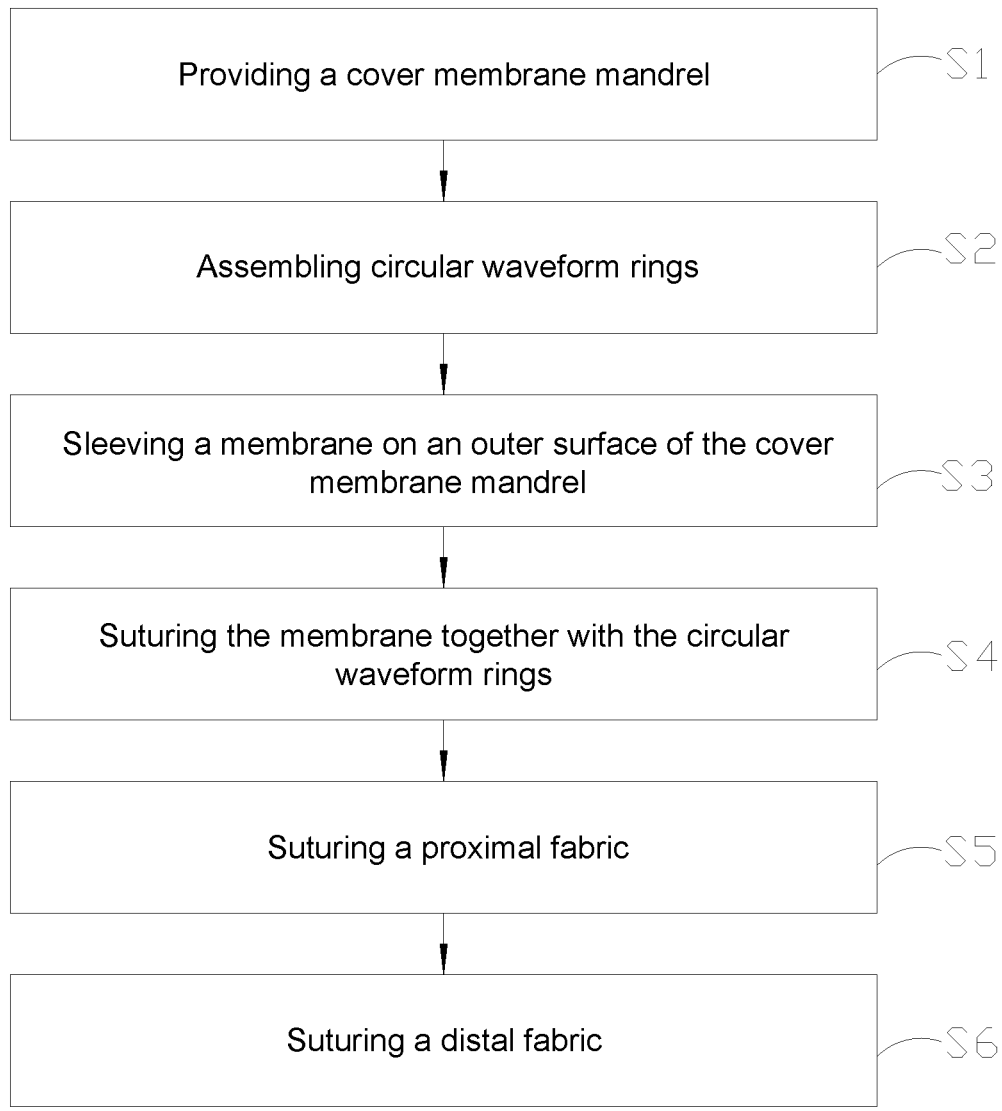
FIG. 16 is a flowchart of a manufacturing method of the aortic arch intraoperative stent provided by the third embodiment of the present invention.

With reference to FIG. 16, a manufacturing method of the aortic arch intraoperative stent provided by a third embodiment of the present invention is nearly the same as that provided by the first embodiment, and the difference from the first embodiment are from steps S2), S3) and S4).

In step S2), several circular waveform rings formed by braiding of elastic nickel-titanium alloy wires are provided, wherein the circular waveform rings of the main body 17 are formed by braiding of elastic nickel-titanium alloy wires with a diameter of 0.55 mm, and the third circular waveform rings 33 of the first branch 5, the second branch 6 and the third branch 7 are respectively formed by braiding of nickel-titanium alloy wires with a diameter of 0.4 mm. Several first circular waveform rings 31 are sleeved in spaced-apart manner on the first column segment 411. Each of the second circular waveform rings is sleeved on the second column segment 412 and located at one side of the second columns 42 which is corresponding to such second circular waveform ring, wherein such side of the second columns 42 is adjacent to the proximal end, so that one waveform 8 of the second circular waveform ring can bypass the corresponding second columns 42. The third circular waveform rings are sleeved in spaced-apart manner on each of the second columns 42, as shown in FIG. 6. Preferably, the embedded depth of each branch of the mandrel embedded in the waveform 8 of the second circular waveform ring may be up to or more than 50% of the height of the waveform 8.

S3) The cover membrane 25, which is polyester fabric or Dacron, is sleeved on the outer surface of the circular waveform rings.

S4) The cover membrane 25 and the circular waveform rings are sutured together through the seams. The polyester fabric at the proximal end 22 of the main body 17 has a portion which is not supported by any circular waveform rings, wherein such portion has a length of 25 to 35 mm (preferably 30 mm) and a diameter slightly smaller than that of the other portions of the main body 17. The polyester fabric at the distal end 23 of the main body 17 has a portion which is not supported by any circular waveform rings, wherein such portion has a length of 8 to 12 mm (preferably 10 mm) and a diameter equal to that of the portion with the circular waveform rings of the main body 17.

The aortic arch intraoperative stent provided by the present invention may automatically adapt to the vascular structure near the aortic arch of different patients, and the main body of the aortic arch intraoperative stent can maintain a sufficient radial support for the branches, thereby ensuring that the branches of the aortic arch intraoperative stent may safely enter branch vessels during surgery, and preventing the branches from slipping out of the corresponding branch vessels during and after surgery. The aortic arch intraoperative stent provided by the present invention has the following advantages.

1) The main body of the aortic arch intraoperative stent in the present invention can provide a reliable support for the branches, thereby ensuring that the branches may completely enter branch vessels, and avoiding the stent from displacing and slipping out postoperative in the future.

2) Due to the complex anatomical structure of the aortic arch, for different patients, there are notable individual differences in the distances between branches. However, the type A aortic dissection of the aortic arch is usually an emergency, and so there is insufficient time to customize a special stent for a patient which is exactly matched with the distance between branches of the patient. The distance between the branches of the aortic arch intraoperative stent in the present invention may be adaptively adjusted according to the anatomical shape of the aortic arch, thus solving the problem that it is difficult for the aortic arch to match with the aortic arch intraoperative stent in emergency surgery due to relatively large individual difference in the shape of the aortic arch of the patients.

3) The main body and the branches of the aortic arch intraoperative stent in the present invention may adopt a double-layer membrane covering technology of integral inner and outer layers of ePTFE membrane, and the inner wall of the branches is smooth, thereby reducing thrombosis and protecting blood vessels in the brain. The main body and the branches are connected without using a suture, so that there is no risk of blood leakage. A proximal fabric is attached on the main body; e.g., a segment of tubular polyester fabric is sewn on the proximal end of the main body, part of region on the proximal end of the polyester fabric is not supported by any metal ring, and the diameter of the polyester fabric in this region is slightly smaller than that of portion of the main body which has the metal scaffold; the polyester fabric ensures reliable anastomosis between the stent and the blood vessels, and the polyester fabric can be prevented from being crinkled during anastomosis with a slightly smaller diameter. In addition, a distal fabric may also be attached on the main body; e.g., a segment of tubular polyester fabric may also be sewn on the distal end of the main body, a small segment of the region on the distal end of the main body may be not supported by any metal ring, and this segment of polyester fabric ensures that the distal end of the main body has a reliable suturing performance, thereby providing guarantee for the long-term surgical treatment.

4) The descending aorta segment of the main body of the aortic arch intraoperative stent in the present invention may be tapered, in order to better adapt to the anatomical shape of the descending aorta segment.

5) One circle of the circular waveform ring on the topmost end of the branches of the aortic arch intraoperative stent in the present invention has densely arranged small waveforms, to ensure optimum apposition performance of the top ends of the branches.

6) One circle of the circular waveform ring on the topmost end of the branches of the aortic arch intraoperative stent in the present invention may be necked down (the diameter of the topmost end is the smallest), the other waveforms are straight tubular-shaped; in this way, the stability of the branches in the branch vessels of the aortic arch is ensured, and the injury to the branch vessels induced by the excessive extension force applied by the branch is also avoided.

7) One circle of the circular waveform ring on the bottommost end of each branch of the aortic arch intraoperative stent in the present invention is necked down (the diameter close to one side of the main body is the smallest), such design may ensure that the branches may freely swing better, in order to better adapt to the anatomical shape differences between the aortic arch and the branch vessels of different patients.

The above descriptions are merely preferred embodiments of the present invention, but not for limiting the present invention. Any modification, equivalent replacement and improvement done within the spirit and principle of the present invention should be regarded as falling into the protection scope of the present invention.

The invention claimed is:
1. An aortic arch intraoperative stent, comprising:
a metallic main body having a distal end and a proximal end, and having at least one branch coupled to the main body; wherein the main body comprises a plurality of self-expanding main body circular waveform rings, and with at least one of the self-expanding main body circular waveform rings corresponding to one of the branches;
a cover membrane that covers the plurality of self-expanding main body circular waveform rings;
a proximal fabric assembly comprising a proximal end, a first layer of tubular proximal fabric, a second layer of proximal fabric, and a third layer of proximal fabric arranged on the proximal end of the main body,
wherein the second layer directly covers the main body with an inner segment which folds over the proximal end of the main body to form a folded segment;
wherein the first layer of tubular proximal fabric comprises a first segment located at the proximal end of the main body, and a second segment extending distally from the first segment and past the main body so that the second segment is a freely extending segment,
wherein the proximal fabric assembly is arranged with the inner segment of the second layer of proximal fabric being the innermost layer lying adjacent the main body and serving as the luminal layer of the stent, the third layer of proximal fabric being the outermost layer and abluminal layer of the stent, the second segment of the first layer being positioned adjacent both the folded segment of the second layer and the third layer of proximal fabric so that the second segment of the first layer extends freely past the second layer of proximal fabric, the third layer of proximal fabric, and the main body.

2. The stent of claim 1, wherein the main body extends in an axial direction and further comprises:
an arch segment and a descending aorta segment, with the branches of the at least one branch located at the arch segment, and wherein the plurality of self-expanding main body circular waveform rings comprise a plurality of descending aorta segment circular waveform rings spaced-apart along the axial direction of the main body along the descending aorta segment; and
first connection rods;
wherein the main body has a circumference, and the branches of the at least one branch are located along one portion of the circumference of the main body, and wherein the first connection rods are located on the one portion of the circumference of the main body, and are connected to the plurality of descending aorta segment circular waveform rings.

3. The stent of claim 2, wherein each of the descending aorta segment circular waveform rings has a diameter, and the diameters of the descending aorta segment circular waveform rings are equal, or gradually decreased from the proximal end to the distal end of the main body.

4. The stent of claim 3, wherein the at least one branch comprises a distal branch that is closest to the descending aorta segment, the distal branch comprising a plurality of branch circular waveform rings that are spaced apart from each other, and a second connection rod is arranged on one side of the distal branch adjacent to the descending aorta segment.

5. The stent of claim 2, wherein each of the branches of the at least one branch comprises a plurality of branch circular waveform rings that are spaced apart from each other, and a second connection rod that is located at one side of the branch adjacent to the proximal end of the main body.

6. The stent of claim 2, further including a tubular distal fabric which is connected to the cover membrane and fixed to the descending aorta segment circular waveform rings, and arranged on the distal end of the main body.

7. The stent of claim 1, wherein each branch comprises a plurality of branch circular waveform rings, and wherein a distance is defined between adjacent pairs of the branch circular waveform rings, with the shortest distance between the branch circular waveform ring closest to the main body and the main body being 4 to 10 mm.

8. The stent of claim 1, wherein each branch comprises a plurality of branch circular waveform rings, and wherein each of the branch circular waveform rings has a waveform height and a waveform number, and wherein each of the branch circular waveform rings farthest from the main body has the smallest waveform height and the largest waveform number.

9. The stent of claim 1, wherein each branch extends in an axial direction, each branch having a first end connected to the main body and a second end farthest from the main body, each branch further comprising a plurality of branch circular waveform rings, each of the plurality of branch circular waveform rings having a diameter, and wherein the diameters of the plurality of branch circular waveform rings are gradually decreased along the axial direction from the first end.

10. The stent of claim 1, wherein each branch extends in an axial direction, each branch having a first end connected to the main body and a second end farthest from the main body, each branch further comprising a plurality of branch circular waveform rings, each of the plurality of branch circular waveform rings having a diameter, and wherein the diameters of the plurality of branch circular waveform rings are gradually decreased along the axial direction from the second end.

11. The stent of claim 1, wherein the cover membrane is made of expanded polytetrafluoroethylene and comprises an inner membrane and an outer membrane, wherein the inner membrane and the outer membrane cover the main body circular waveform rings.

12. The stent of claim 1, wherein the cover membrane is made of polyester fabric and defines a tubular wall, and the main body circular waveform rings are sutured on an outer side or an inner side of the tubular wall of the cover membrane.

13. The stent of claim 1, wherein the at least one main body circular waveform ring comprises at least two main body circular waveform rings that are connected to each other without using a connection rod.

14. The stent of claim 1, wherein a distance is defined between adjacent main body circular waveform rings, and the shortest distance between two adjacent main body circular waveform rings is 2 to 8 mm.

15. The stent of claim 1, wherein the first layer of proximal fabric is prepared from ribbed polyester fabric.

16. The stent of claim 1, wherein the second segment of the first layer of tubular proximal fabric has a distal end, and the distal end of the second segment is located at a distal side of one of the branches.

17. The stent of claim 1, wherein both the first and second segments of the first layer of tubular proximal fabric have a diameter, and the diameter of the first segment is smaller than that of the second segment.

18. The stent of claim 1, wherein the number of self-expanding main body circular waveform rings is identical to the number of branches.

* * * * *